United States Patent
Wiley et al.

(10) Patent No.: US 10,182,986 B2
(45) Date of Patent: Jan. 22, 2019

(54) METHOD OF DELIVERING THERAPEUTICS AND IMAGING AGENTS TO THE BRAIN BY NANOPARTICLES THAT CROSS THE BLOOD BRAIN BARRIER

(71) Applicant: CALIFORNIA INSTITUTE OF TECHNOLOGY, Pasadena, CA (US)

(72) Inventors: Devin Wiley, Pasadena, CA (US); Andrew Clark, Pasadena, CA (US); Mark E. Davis, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/358,206

(22) Filed: Nov. 22, 2016

(65) Prior Publication Data

US 2017/0071857 A1 Mar. 16, 2017

Related U.S. Application Data

(63) Continuation of application No. 14/120,309, filed on May 14, 2014.

(60) Provisional application No. 61/822,983, filed on May 14, 2013.

(51) Int. Cl.
| | |
|---|---|
| *A61K 9/00* | (2006.01) |
| *A61K 31/4045* | (2006.01) |
| *A61K 31/137* | (2006.01) |
| *A61K 51/12* | (2006.01) |
| *A61K 47/59* | (2017.01) |
| *A61K 47/64* | (2017.01) |
| *A61K 47/69* | (2017.01) |

(52) U.S. Cl.
CPC .......... *A61K 9/0085* (2013.01); *A61K 9/0019* (2013.01); *A61K 31/137* (2013.01); *A61K 31/4045* (2013.01); *A61K 47/593* (2017.08); *A61K 47/644* (2017.08); *A61K 47/6923* (2017.08); *A61K 47/6935* (2017.08); *A61K 47/6937* (2017.08); *A61K 51/1244* (2013.01)

(58) Field of Classification Search
None
See application file for complete search history.

(56) References Cited

U.S. PATENT DOCUMENTS

| | | | |
|---|---|---|---|
| 4,631,190 A | 12/1986 | Shen et al. | |
| 5,972,707 A * | 10/1999 | Roy | A61K 9/167 435/320.1 |
| 8,367,116 B2 | 2/2013 | Pratt | |
| 9,132,097 B2 | 9/2015 | Davis et al. | |
| 2002/0054902 A1 | 5/2002 | Pardridge | |
| 2003/0147966 A1 | 8/2003 | Franzen et al. | |
| 2004/0126838 A1 | 7/2004 | DeFrees et al. | |
| 2009/0281024 A1 | 11/2009 | Zankel et al. | |
| 2010/0040556 A1 | 2/2010 | Davis et al. | |
| 2010/0069500 A1 | 3/2010 | Dhal et al. | |
| 2010/0166865 A1 | 7/2010 | Kumar et al. | |
| 2012/0225129 A1 | 9/2012 | Eiiasof et al. | |
| 2012/0259021 A1 | 10/2012 | Jiang et al. | |
| 2012/0309691 A1 | 12/2012 | Zhou et al. | |
| 2012/0328564 A1 | 12/2012 | Govindan et al. | |

FOREIGN PATENT DOCUMENTS

| | | |
|---|---|---|
| JP | 2000-514440 | 10/2000 |
| JP | 2004-525858 A | 11/2001 |
| JP | 2005-511761 | 4/2005 |
| JP | 2010-501004 A | 5/2008 |
| JP | 2009-508494 | 3/2009 |
| JP | 2012-500208 A | 2/2010 |
| WO | 01/82900 A1 | 11/2001 |
| WO | 2008/060734 A2 | 5/2008 |
| WO | WO 2010/019718 A2 | 2/2010 |
| WO | WO 2011/072133 A1 | 6/2011 |
| WO | WO 2012/079047 A2 | 6/2012 |
| WO | WO 2012/158622 A2 | 11/2012 |

OTHER PUBLICATIONS

Kale et. al. "Design, Synthesis, and Characterization of pH-Sensitive PEG-PE Conjugates for Stimuli-Sensitive Pharmaceutical Nanocarriers: The Effect of Substitutes at the Hydrazone Linkage on the pH Stability of PEG-PE Conjugates", Bioconjugate Chem. 2007, 18, 363-370 (Year: 2007).*
Armstrong et al., "The Hydrodynamic Radii of Macromolecules and Their Effect on Red Blood Cell Aggregation", Biophysical Journal, 2004, 87(6), 4259-4270.
Bao et al., "OX26 modified hyperbranched polyglycerol-conjugated poly(lactic-co-glycolic acid) nanoparticles: Synthesis, characterization and evaluation of its brain delivery ability", Journal of Materials Science: Materials in Medicine, May 9, 2012, vol. 23, No. 8, 1891-1901.
Bartlett et al., "Physicochemical and Biological Characterization of Targeted, Nuclic Acid-Containing Nanoparticles", Bioconjug Chem, 2007, 18, 456-468.
Bellocq et al., "Transferrin-Containing Cyclodextrin Polymer-Based Particles for Tumor-Targeted Gene Delivery", Bioconjug Chem, 2003, 14, 1122-1132.
Chang et al., "Characterization of endocytosis of transferrin-coated PLGA nanoparticles by the blood-brain barrier", International Journal of Pharmaceutics, Sep. 11, 2009, vol. 379, No. 2, 285-292.
Choi et al., "Mechanism of Active Targeting in Solid Tumors With Transferrin-Containing Gold Nanoparticles", P Natl Acad Sci, 2010, 107(3), 1235-1240.
Choi et al., "Targeting Kidney Mesangium by Nanoparticles of Defined Size", P Natl Acad Sci, 2001, 108, 6656-6661.

(Continued)

*Primary Examiner* — James W Rogers
(74) *Attorney, Agent, or Firm* — Baker & Hostetler LLP

(57) ABSTRACT

Described herein are methods of delivering a nanoparticle across the blood brain barrier to the brain of a subject by administering to the subject a nanoparticle having a nanoparticle core and a targeting agent. A variety of targeting agents may serve to promote delivery of the described nanoparticle.

24 Claims, 22 Drawing Sheets

(56) References Cited

OTHER PUBLICATIONS

Dautry-Varsat et al., "pH and the Recycling of Transferrin During Receptor-Mediated Endocytosis", P Natl Acad Sci, 1983, 80, 2258-2262.
Davis et al., "Evidence of RNAi in Humans from Systemically Administered siRNA Via Targeted Nanoparticles", Nature, 2010, 464, 1067-1070.
Davis et al., "Nanoparticle Therapeutics: An Emerging Treatment Modality for Cancer", Nature Rev., 2008, 7, 771-782.
Davis, "The First Targeted Delivery of siRNA in Humans Via a Self-Assembling, Cyclodextrin Polymer-Based Nanoparticle: From Concept to Clinic", Molecular Pharm., 2009, 6(3), 659-668.
Friden et al., "Characterization, Receptor Mapping and Blood-Brain Barrier Transcytosis of Antibodies to the Human Transferrin Receptor", J Pharm Exp Ther, 1996, 278, 1491-1498.
Hou et al., "Development of Zeptomole and Attomolar Detection Sensitivity of Biotin-Peptide Using a Dot-Blot GoldNanoparticle Immunoassay", Anal. Chem., 2007, 79(3), 980-985.
International Patent Application No. PCT/US14/00099: International Search Report and Written Opinion dated Aug. 19, 2014, 17 pages.
Jiang et al., "Nanoparticle-Mediated Cellular Response is Size-Dependent", Nature Nanotech, 2008, 3(3), 145-150.
Kamaly et al., "Targed Polymeric Therapeutic Nanoparticles: Design, Development and Clinical Translation", Chem Soc. Rev, 2012, 41, 2971.
Lockman et al., "Nanoparticle Surface Charges Alter Blood-Brain Barrier Integrity and Permeability", J Drug Target, 2004, 12(9-10), 635-641.
Lundqvist et al., "Nanoparticle Size and Surface Properties Determine the Protein Corona with Possible Implications for Biological Impacts", P Natl Acad Sci, 2008, 105, 14265-14270.
Mangani et al., "EXAFS Studies on Copper Transferrin", J Inorganic Biochem, 1992, 48(1), 33-40.
Martinez-Veracoechea et al., "Desining Super Selectivity in Multivalent Nano-Particle Binding", P Natl Acad Sci USA, 2011, 108(27), 10963-10968.
Montet et al., Multivalent Effects of RGD Peptides Obtained by Nanoparticle Display, J. Med. Chem., 2006, 49(20), 6087-6093.
Nance et al., "A Dense Poly(Ethylene Glycol) Coating Improves Penetration of Large Polymeric Nanoparticles Within Brain Tissue", Sci Transl Med, 2012, 4(149), 149ra119.
Neuwelt et al., "Strategies to Advance Translational Research into Brain Barriers", Lancet Neurol, 2008, 7(1), 84-96.
Pardridge, "The Blood-Brain Barrier: Bottleneck in Brain Drug Development", NeuroRX, 2005, 2(1), 3-14.
Perrault et al., "Mediating Tumor Targeting Efficiency of Nanoparticles Through Design", Nano Lett, 2009, 9(5), 1909-1915.
Prades et al., "Delivery of gold nanoparticles to the brain by conjugation with a peptide that recognizes the transferrin receptor", Biomaterials, 2012, 33, 7194-7205.
Wiley et al., "Trancytosis and Brain Uptake of Transferrin-Containing Nanoparticles by Tuning Avidity to Transferrin Receptor", P Natl Acad Sci, 2013, 1-6.
Wolburg et al., "Epithelial and Endothelial Barriers in the Olfactory Region of the Nasal Cavity of the Rat", Histochem Cell Biol, 2008, 130(1), 127-140.
Xiao et al., "The Effect of Surface Charge on In Vivo Biodistribution of PEG-Oligocholic Acid Based Micellar Nanoparticles", Biomaterials, 2011, 32, 3435-3446.
Yu et al., "Boosting Brain Uptake of a Therapeutic Antibody by Reducing Its Affinity for a Transcytosis Target", Sci Transl Med, 2011, 3(84), 1-8.
Van Rooy et al., "Identification of Peptide Ligands for Targeting the Blood-Brain Barrier", Pharmaceutical Research, Apr. 2010, 27(4), 673-682.
Schluep et al., "Pharmacokinetics and tumor dynamics of the nanoparticle IT-101 from PET imaging and tumor histological measurements", PNAS, Jul. 7, 2009, vol. 106, No. 27, 11394-11399.
Saraiva et al., "Nanoparticle-mediated brain drug delivery: Overcoming—blood-brain barrier to treat neurodegenerative diseases", Journal of Controlled Release, 2016, 235, 34-47.
Pardridge, "Blood-Brain Barrier Drug targeting: The Future of Brain Drug Development", Molecular Interventions, Mar. 2003, vol. 3, No. 2, 90-105.
Hanmei Bao et al: "0×26 modified hyperbranched polyglycerolconjugated poly(lactic—glycolic acid) nanoparticles: synthesis, characterization and evaluation of its brain delivery ability", Journal of Materials Science: Materials in Medicine, Kluwer Academic Publishers, BO, vol. 23, No. 8, May 9, 2012 (May 9, 2012), pp. 1891-1901.
Georgieva et al., "Smuggling Drugs into the Brain: An Overview of Ligands Targeting Transcytosis for Drug Delivery Across the Blood Brain Barrier", Pharmaceutics, 2014, 6(4), 557-583.
D. T. Wiley et al: "Transcytosis and brain uptake of transferrincontaining nanoparticles by tuning avidity to transferrin receptor", Proceedings of the National Academy of Sciences, vol. 110, No. 21, May 6, 2013 (May 6, 2013), pp. 8662-8667.
Cerqueira-Coutinho et al., "Comparison of biodistribution profile of monoclonal antibodies nanoparticles and aptamers in rats with breast cancer", Artificial Cells, Nanomedicine, and Biotechnology, 2017, vol. 45, No. 3, 598-601.
Bartlett et al., "Impact of tumor-specific targeting on the biodistribution and efficacy of siRNA nanoparticles measured by multimodality in vivo imaging", PNAS, Sep. 25, 2007, vol. 104, No. 39, 15549-11154.

* cited by examiner

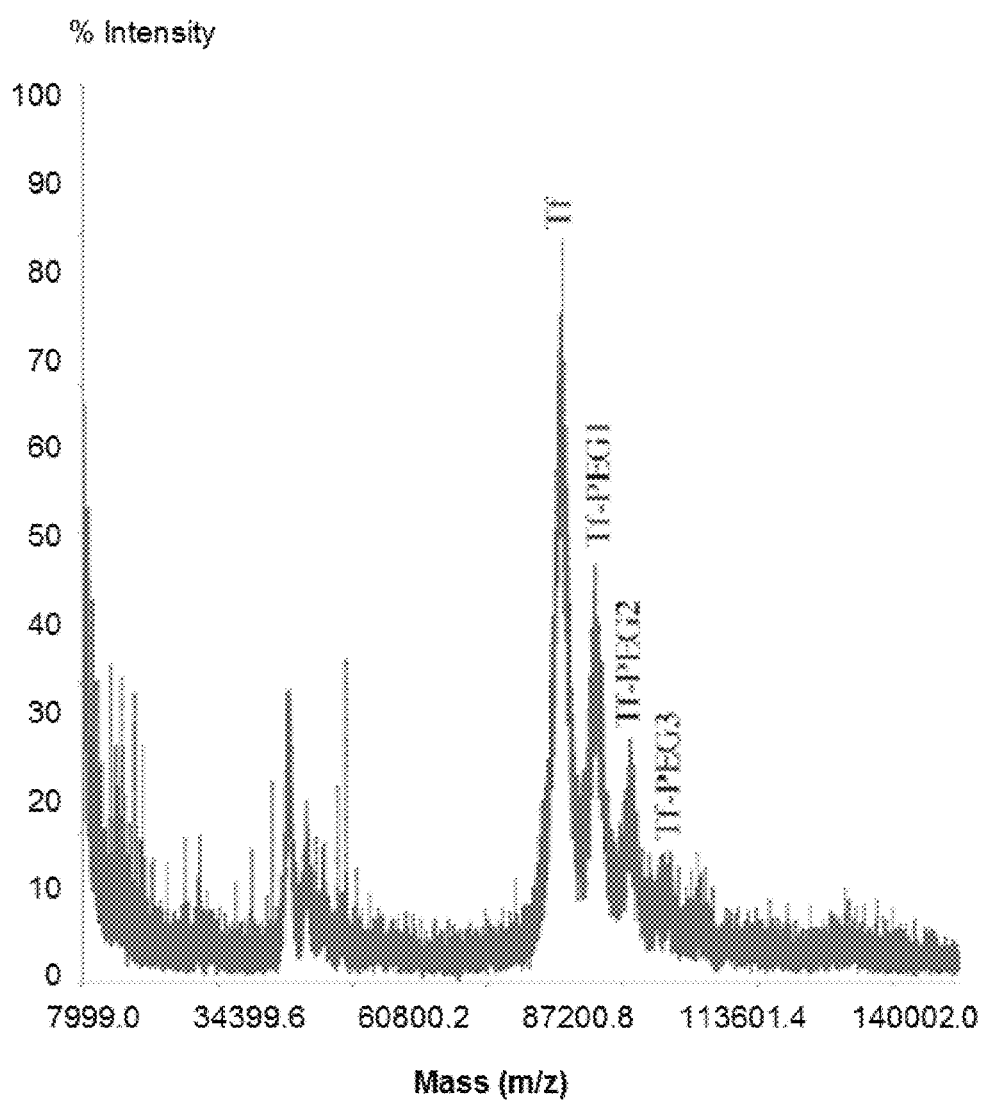

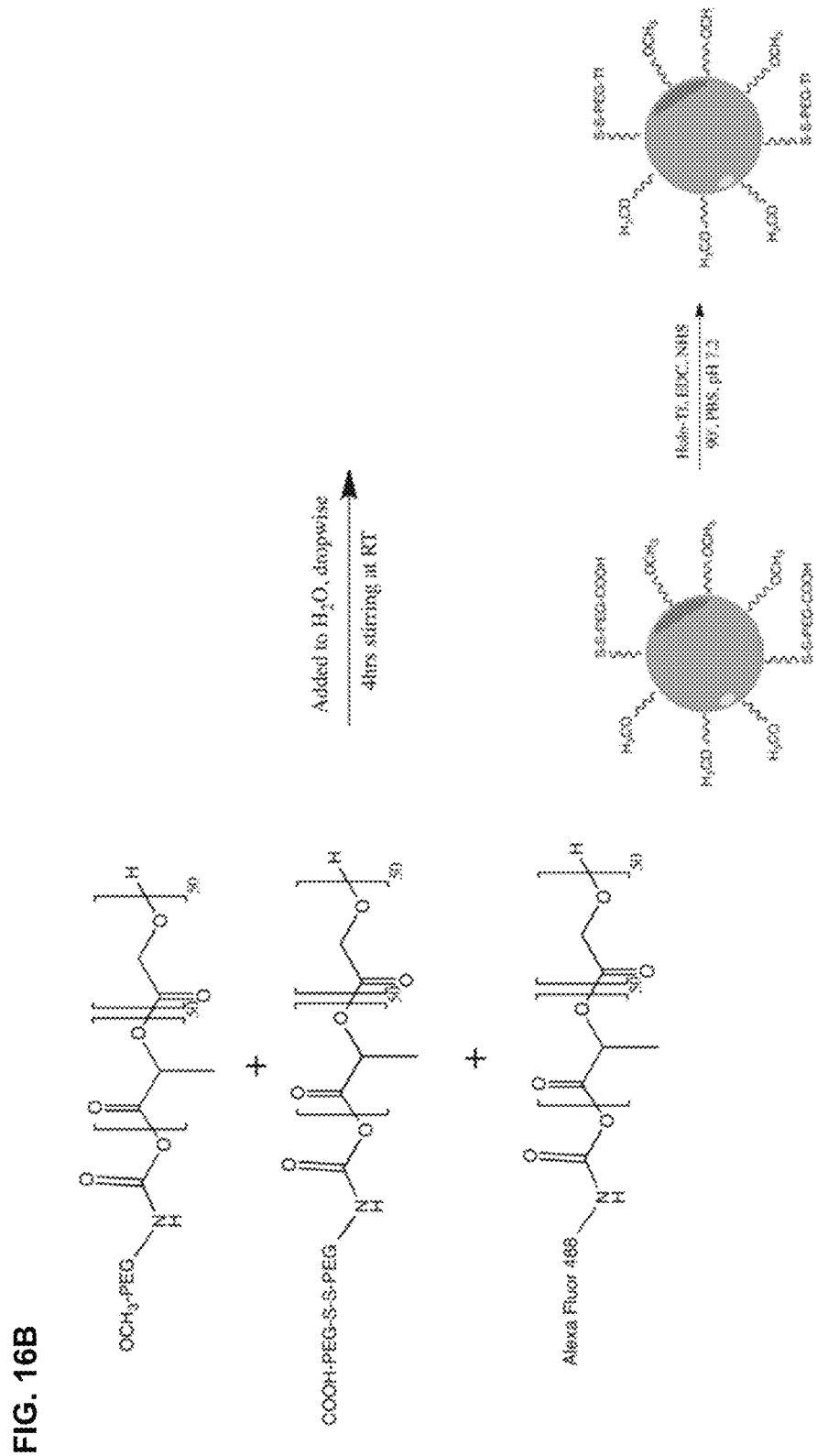

METHOD OF DELIVERING THERAPEUTICS AND IMAGING AGENTS TO THE BRAIN BY NANOPARTICLES THAT CROSS THE BLOOD BRAIN BARRIER

CROSS REFERENCE TO RELATED APPLICATIONS

This application is a continuation of U.S. patent application Ser. No. 14/120,309, filed May 14, 2014, which claims the benefit of U.S. Provisional Patent Application 61/822,983, filed on May 14, 2013, the entire contents of each of which is incorporated by reference herein.

GOVERNMENT RIGHTS

This invention was made with government support under Grant No. NS071112 and Grant No. CA151849 awarded by the National Institutes of Health. The Government has certain rights in the invention.

BACKGROUND

Chronic diseases of the central nervous system (CNS) are a major cause of morbidity and mortality in the developed world. Alzheimer's disease alone affects over five million people in the United States, and is expected to increase to over thirteen million by 2050. The estimated total cost of care in 2012 for people with Alzheimer's disease was over $200 billion and is expected to rise to $1.2 trillion within the next forty years. Moreover, while the proportion of deaths from many other leading causes of mortality in the United States, such as heart disease and stroke, have seen significant decreases over the last decade, the proportion of deaths from Alzheimer's disease has increased 68%. A similar trend, in both high economic cost and a relative lack of progress in treatment, is seen with many other neurodegenerative diseases, including Huntington's disease, Parkinson's disease, and multiple sclerosis.

A major reason for the lack of progress in treating these diseases is due to the presence of the blood-brain barrier (BBB). The BBB is a physical barrier between the CNS parenchyma and vasculature that plays a critical role in maintaining homeostasis within the CNS. Tight junctions exist between endothelial cells that inhibit paracellular diffusion of polar molecules, macromolecules and cells. This forces solute transport into the CNS to occur primarily across individual endothelial cells. Though critically important for maintaining CNS homeostasis, the impermeability of the BBB to most solutes has proven a tremendous obstacle for drug delivery to the CNS. Currently, 98% of small molecule therapeutics and essentially 100% of large-molecule therapeutics, including, monoclonal antibodies, proteins and gene therapies, do not cross the BBB.

Of the several endogenous methods used by solutes to cross the BBB, receptor-mediated transcytosis (RMT) has shown the most promise for use in drug delivery (see, Wiley et al., PNAS, 110(21):8662-667 (2013), which is incorporated by reference herein in its entirety). Although there has been much interest over the past two decades in developing targeted therapeutics for delivery to the brain, there is yet to emerge a viable candidate for clinical investigation.

SUMMARY

Described herein are methods of delivering a nanoparticle to the brain of a subject by administering to the subject a nanoparticle having a nanoparticle core and a targeting agent. A variety of targeting agents may serve to promote delivery of the described nanoparticle. For example, the targeting agent may include a ligand specific for a receptor expressed by brain endothelial cells and a linker that connects the ligand to the external surface of the nanoparticle core. Additionally, the linker can promote disassociation of the ligand from the nanoparticle when inside a cell.

The described methods can be carried out using a variety of nanoparticles. For example, the surface of the nanoparticle core can be made of cationic mucic acid polymers (cMAP), poly(lactic-co-glycolic acid) (PLGA), chitosan, synthetic polymers such as polyethyleneimine, gold, iron oxide, or other analogous material as understood by those skilled in the art. These polymers can be combined with a ligand such as transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, or a polypeptide that specifically binds to the insulin-like growth factor receptor 1. Additionally, the nanoparticle core and ligand can be conjugated by a linker that can facilitate disassociation of the ligand from the nanoparticle when inside a brain endothelial cell. In some of the described embodiments the linker may include a disulfide bond that can be reduced to cause disassociation of the ligand from the nanoparticle when the nanoparticle is inside a brain endothelial cell. In some of the described embodiments the linker may include a polypeptide that can be enzymatically cleaved to cause disassociation of the ligand from the nanoparticle when the nanoparticle is inside a brain endothelial cell. In some of the described embodiments the linker may include a hydrolyzable chemical bond that can be disrupted at low pH to cause disassociation of the ligand from the nanoparticle when the nanoparticle is inside a brain endothelial cell. In some of the described embodiments the linker may include a chemical bond having a pKa that can be disrupted at low pH to cause disassociation of the ligand from the nanoparticle when the nanoparticle is inside a brain endothelial cell.

The provided methods may be carried out with targeting agents making use of a variety of linkers for conjugating the ligand to the nanoparticle core and for facilitating disassociation of the ligand from the nanoparticle once inside a brain endothelial cell. In some embodiments the described methods can be carried out using a linker having a nitrophenyl boronic acid when unbound to the nanoparticle that forms a nitrophenyl boronic ester to bind to the nanoparticle core, where decoupling of the linker and the nanoparticle core will be favored at acidic pH (e.g., about 6.8 to about 2.0). In another embodiment the targeting agent may include a diamino ketal (DAK) linkage to facilitate disassociation of the nanoparticle and the ligand once inside a brain endothelial cell, where decoupling of the linker and the nanoparticle core will be favored at acidic pH. Additionally, the described methods may be carried out using a targeting agent with a linker having a disulfide bond that can facilitate disassociation of an attached ligand from the nanoparticle under reducing conditions encountered in a brain endothelial cell. In some of the described embodiments the targeting agent includes a polyethylene glycol polymer in between the ligand and the segment that mediates conjugation to the nanoparticle core.

To carry out the described methods it may be advantageous to control the number of targeting agents that are conjugated to the described nanoparticles. In some embodiments the described nanoparticles may have as many as 1000 conjugated targeting agents. In other embodiments the described nanoparticles may have as many as 500 conjugated targeting agents. Alternatively, the described nanoparticles may have as few as from about 20 to 50 conjugated targeting agents. In yet another embodiment the described nanoparticles may have less than 5 conjugated targeting agents. The number of targeting agents may be modulated depending on the type of nanoparticle being delivered, the delivery target, the ligand used to target the particle, or a host of other factors.

The described method may be used to deliver therapeutic or imaging agents to the brain of a subject, by loading the described nanoparticles with a therapeutic agent or imaging agent of interest prior to administration of the nanoparticle to the subject. Following delivery of the loaded nanoparticle, the targeting agent will facilitate delivery to a target cell of interest, such as a brain endothelial cell. Following internalization by the target cell, the nanoparticle will dissociate from the targeting agent. In the case of brain endothelial cells, the internalized nanoparticle will then be excreted from the cell into the interstitial space of the brain where the particle will destabilize and secrete the loaded agent, thereby delivering the agent to the brain or other target location. In some embodiments the described methods may be carried out to deliver a neurotransmitter such as serotonin or dopamine to the brain, which may be used to treat a neurological disorder. Other agents for use in treating neurological disorders may also be delivered to the brain via the described methods. Imaging agents that might not readily access the brain on their own may also be delivered using the described methods. Further, the described methods may be used to deliver a combination of one or more therapeutic agents, imaging agents, or both therapeutic agents, imaging agent to the brain of a subject.

Also described herein are kits for producing a nanoparticle targeted for delivery to the brain. For example, the described kits may contain the materials and reagents to assemble nanoparticles having a cationic mucic acid polymer (cMAP) exterior surface or a poly(lactic-co-glycolic acid) (PLGA) exterior surface, a targeting agent specific for a receptor expressed by brain endothelial cells, wherein the targeting agent includes a ligand that is conjugated to a linker that causes disassociation of the ligand from the nanoparticle when inside a brain endothelial cell; and instructions for assembling the nanoparticle. The described kits may also include a ligand for targeting brain endothelial cell, such as transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, or a polypeptide that specifically binds to the insulin-like growth factor receptor 1.

BRIEF DESCRIPTION OF THE DRAWINGS

FIGS. 11A-F show Tf-DAK-PEG-OPSS degradation in pH 5.5 buffer over time. Composition of the crude mixture is shown at 5 min (FIG. 11A), 15 min (FIG. 11B), 30 min (FIG. 11C), 60 min (FIG. 11D), 120 min (FIG. 11E) and 24 hrs (FIG. 11F) incubation time.

FIG. 16B shows the preparation of disulfide-containing nanoparticles. Each polymer mixture was prepared in DMF at a total PLGA concentration of 10 mg/mL prior to formation of the nanoparticles through nanoprecipitation.

DETAILED DESCRIPTION OF ILLUSTRATIVE EMBODIMENTS

Figure 1:
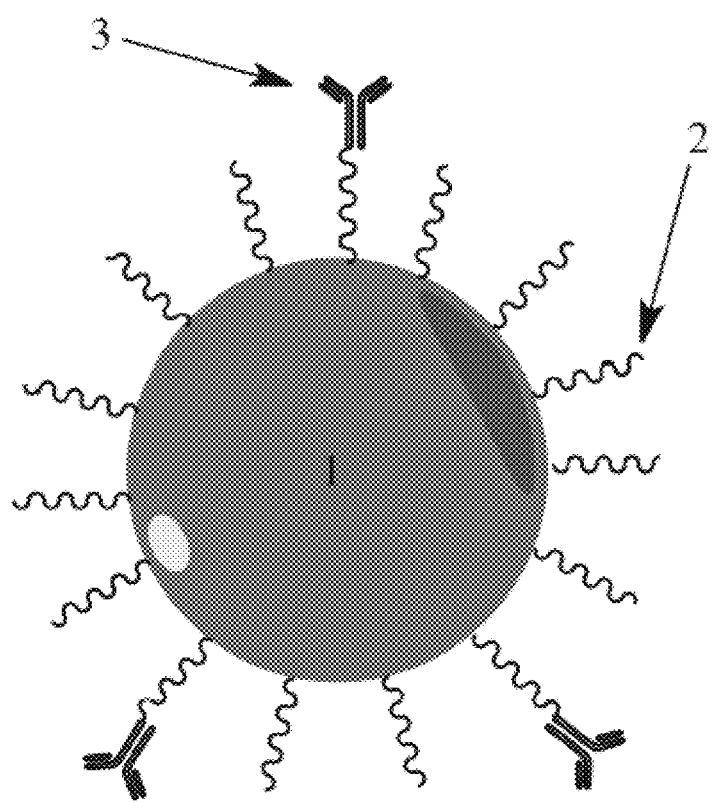
FIG. 1. General design of a nanoparticle for the delivery of a therapeutic and/or imaging agent to the brain parenchyma. The nanoparticle has three fundamental design components: (1) the nanoparticle core; (2) a spacing molecule; and (3) a targeting agent.
Figure 2:
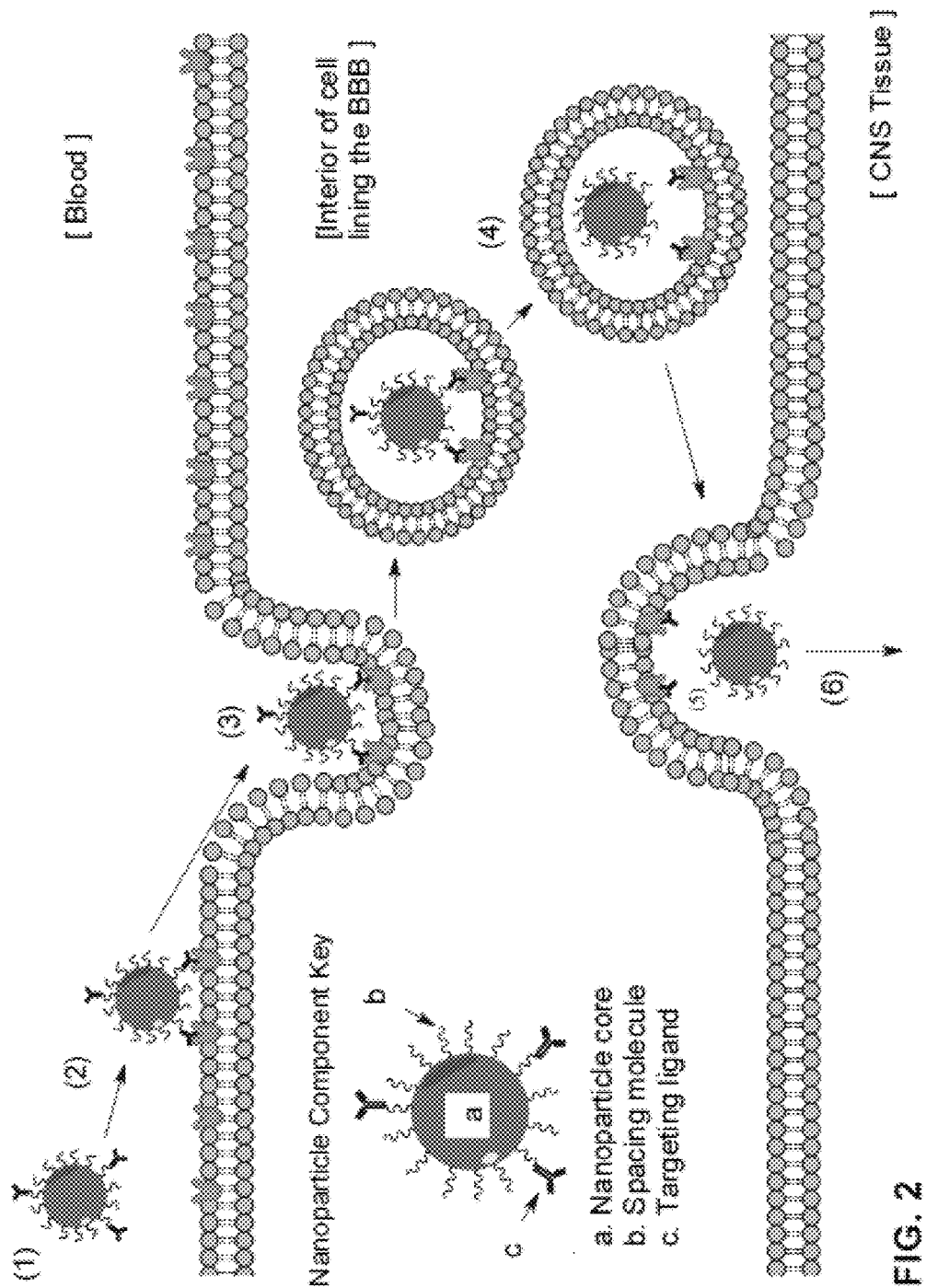
FIG. 2. Transit of targeted nanoparticle through the blood-brain barrier (BBB) facilitated by targeting molecules falling off the nanoparticle. (1) Targeted nanoparticle in the blood reaches the BBB luminal surface. (2) Nanoparticle ligand binds to its receptor on the blood side of the BBB. (3) Internalization of the receptor-nanoparticle complex. (4) Chemical and/or physical changes experienced by the nanoparticle as it crosses the BBB cause detachment of the ligand from the rest of the nanoparticle. (5) The untargeted nanoparticle reaches the brain side of the BBB. (6) The nanoparticle diffuses into the CNS. Components of the nanoparticle are identified in the inset key on the left of the figure. Terms in the brackets on the right side of the figure indicate relative compartments involved in this sequence.

Provided herein are methods of delivering nanoparticles to the brain of a subject, also described are nanoparticles and related compositions, methods, and kits that can be used in connection for delivering the described nanoparticles or a compound of interest contained in the nanoparticles.

The term "about" when used in reference to numerical ranges, cutoffs, or specific values is used to indicate that the recited values may vary by up to as much as 10% from the listed value. As many of the numerical values used herein are experimentally determined, it should be understood by those skilled in the art that such determinations can, and often times, will vary among different experiments. The values used herein should not be considered unduly limiting by virtue of this inherent variation. The term "about" is used to encompass variations of this sort up to, or equaling 10%.

The term "nanoparticle" as used herein indicates a composite structure of nanoscale dimensions. In particular, nanoparticles are typically particles of a size in the range of from about 1 to about 1000 nm, and are usually spherical although different morphologies are possible depending on the nanoparticle composition. The portion of the nanoparticle contacting an environment external to the nanoparticle is generally identified as the surface of the nanoparticle. In nanoparticles herein described, the size limitation can be restricted to two dimensions and so that nanoparticles herein described include composite structure having a diameter from about 1 to about 1000 nm, where the specific diameter depends on the nanoparticle composition and on the intended use of the nanoparticle according to the experimental design. For example, nanoparticles to be used in several therapeutic applications typically have a size of about 200 nm or below, and the ones used, in particular, for delivery associated to cancer treatment typically have a diameter from about 1 to about 100 nm.

Additional desirable properties of the nanoparticle, such as surface charges and steric stabilization, can also vary in view of the specific application of interest. Properties of the particles may be understood by a skilled person upon reading of the present disclosure. Nanoparticle dimensions and properties can be detected by techniques known in the art. Exemplary techniques to detect particles dimensions include but are not limited to dynamic light scattering (DLS) and nanoparticle tracking analysis (NTA) and a variety of microscopies such at transmission electron microscopy (TEM) and atomic force microscopy (AFM). Exemplary techniques to detect particle morphology include but are not limited to TEM and AFM. Exemplary techniques to detect surface charges of the nanoparticle include but are not limited to zeta potential method. Additional techniques suitable to detect other chemical properties comprise by $^{1}$H, $^{11}$B, and $^{13}$C and $^{19}$F NMR, UV/Vis and infrared/Raman spectroscopies and fluorescence spectroscopy and microscopy (when nanoparticle is used in combination with fluorescent labels) and additional techniques identifiable by a skilled person.

The term "deliver" and "delivery" as used herein indicates the activity of affecting the spatial location of a compound, and, in particular, specifying the preferred location of a compound. Accordingly, delivering a compound in the sense of the present disclosure indicates the ability to affect positioning and movement of the compound at a certain time under a certain set of conditions, so that the compound's positioning and movement under those conditions are altered with respect to the positioning and movement that the compound would otherwise have.

The term "target" as used herein indicates a biological system of interest including organs, tissues, or any portion thereof and may include in vitro or in vivo biological systems or any portion thereof.

The term a "polymer" as used herein indicates a large molecule composed of repeating structural units typically connected by covalent chemical bonds. A suitable polymer may be a linear and/or branched, and can take the form of a homopolymer or a co-polymer. If a co-polymer is used, the co-polymer may be a random copolymer or a branched co-polymer. Exemplary polymers comprise water-dispersible and in particular water soluble polymers. For example, suitable polymers include, but are not limited to polysaccharides, polyesters, polyamides, polyethers, polycarbonates, polyacrylates, etc. For therapeutic and/or pharmaceutical uses and applications, the polymer should have a low toxicity profile and in particular that are not toxic or cytotoxic. Suitable polymers include polymers having a molecular weight of about 500,000 or below. In particular, suitable polymers can have a molecular weight of about 100,000 and below.

The term "polymer containing a boronic acid" or a "linker having a boronic acid" and the like as used herein indicate containing at least one boronic acid group presented for binding to a hydroxyl group of a polymer containing polyols. In particular, polymers containing boronic acids of the nanoparticles herein described include a polymer comprising in at least one structural unit an alkyl or aryl substituted boronic acid containing a carbon to boron chemical bond. Suitable boronic acid polymers comprise polymers wherein boronic acid is in a terminal structural unit or in any other suitable position to provide the resulting polymer with hydrophilic properties. In the nanoparticles herein described polyols polymers are coupled to the boronic acid polymers. The term "coupled" or "coupling" as used herein with reference to attachment between two molecules indicates an interaction forming a reversible covalent linkage. In particular, in presence of a suitable medium, a boronic acid presented on the boronic acid polymer interact with hydroxyl groups of the polyols via a rapid and reversible pair-wise covalent interaction to form boronic esters in a suitable medium. Suitable medium include water and several aqueous solutions and additional organic media identifiable by a skilled person. In particular, when contacted in an aqueous medium boronic acid polymers and polyols polymers react, producing water as a side product. The boronic acid polyol interaction is generally more favorable in aqueous solutions but is also known to proceed in organic media. In addition, cyclic esters formed with 1,2 and 1,3 diols are generally more stable than their acyclic ester counterparts.

The term "attach", "attached" or "attachment" as used herein, refers to connecting or uniting by a bond, link, force or tie in order to keep two or more components together, which encompasses either direct or indirect attachment such that for example where a first compound is directly bound to a second compound, and the embodiments wherein one or more intermediate compounds, and in particular molecules, are disposed between the first compound and the second compound.

The term "ligand" or "targeting ligand" as used in the present disclosure indicates any molecule that can be presented on the surface of a nanoparticle for the purpose of engaging a specific target, and in particular specific cellular recognition, for example by enabling cell receptor attachment of the nanoparticle. Examples of suitable ligands include, but are not limited to, vitamins (e.g. folic acid), proteins (e.g. transferrin, and monoclonal antibodies), monosaccharides (e.g. galactose), peptides, and polysaccharides. In particular targeting ligands can be antibodies against certain surface cell receptors such as transferrin receptor ("TfR").

As used herein, the term "transferrin" (abbreviated "Tf") is meant to encompass variants and isoforms of the protein, as well as fragments of the protein capable of binding to the transferrin receptor ("TfR"). For example, the term would include holo-transferrin as well as transferrin itself.

The term "antibody" includes reference to an immunoglobulin molecule that is reactive with a particular antigen. The term also includes genetically engineered forms such as chimeric antibodies (e.g., humanized murine antibodies), heteroconjugate antibodies (e.g., bispecific antibodies) and recombinant single chain Fv fragments (scFv), disulfide stabilized (dsFv) Fv fragments, or pFv fragments. The term "antibody" also includes antigen binding forms of antibodies (e.g., Fab', F(ab')2, Fab, Fv and rIgG). An antibody immunologically reactive with, or "specific for," a particular antigen is a relative term and means that the antibody binds to that antigen with an affinity that is at least 10-old higher than would be observed for non-specific binding exhibited by the antibody. Thus, an antibody said to be "specific for" a given antigen may in fact selectively bind other antigens with an affinity that is 10-foldhigh than it exhibits in nonspecific interactions.

It is necessary to develop a targeted therapeutic capable of reaching the CNS in larger amounts in order to treat a large number of debilitating neurological diseases. It may be possible to take advantage of chemical changes experienced during RMT to increase accumulation of therapeutics within the CNS. Described herein are methods of delivering a nanoparticle to the brain of a subject by administering to the subject a nanoparticle having a nanoparticle core and a targeting agent. A variety of targeting agents may serve to promote delivery of the described nanoparticle. For example, the targeting agent may include a ligand specific for a receptor expressed by brain endothelial cells and a linker that connects the ligand to the external surface of the nanoparticle core. Additionally, the linker can promote disassociation of the ligand from the nanoparticle when inside a cell.

The described methods can be carried out using a variety of nanoparticles. For example, the surface of the nanoparticle core can be made of cationic mucic acid polymers (cMAP). In some embodiments the described cMAP nanoparticle cores may be made of a cMAP having a structure represented by any one of the following:

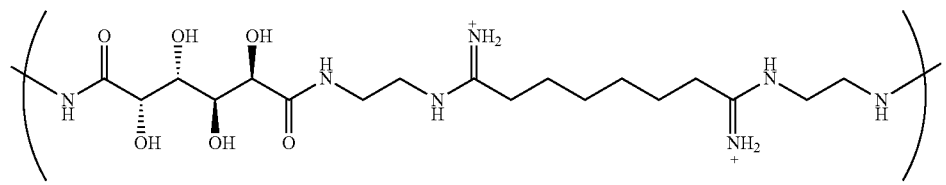

Formula I

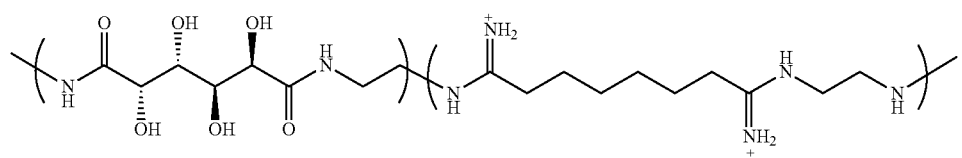

Formula II

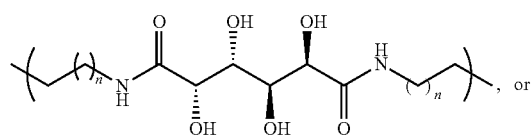, or

Formula III

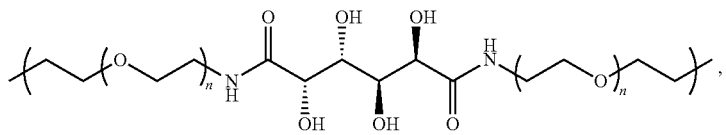

Formula IV where n is any whole number from 2 to about 20. In some embodiments n is any whole number from 2 to about 10. In some embodiments n is any whole number from 2 to about 5. In some embodiments n is 2, 3, or 4.

The cMAP used to produce the described nanoparticle core may have the structure of Formula V:

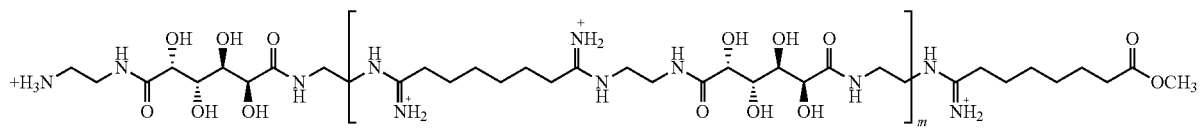

where m is any whole number from 5 to about 200. In some embodiments m is any whole number from 5 to about 150. In some embodiments m is any whole number from 5 to about 100. In some embodiments m is any whole number from 5 to about 50. In some embodiments m is any whole number from 5 to about 25. In some embodiments m may be any one of 5, 6, 7, 8, 9, 10, 11, 12, 13, 14, 15, 16, 17, 18, 19, or 20. As provided herein, in some embodiments m is 11.

In some embodiments of the described methods the nanoparticles are made with a core of poly(lactic-co-glycolic acid) (PLGA) polymers. The PLGA polymers may have a structure of Formula VI:

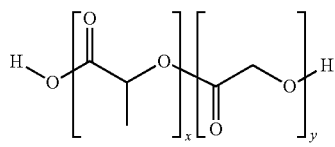

where x and y are, independent of one another, any whole number from about 5 to about 500. In some embodiments x and y are, independent of one another, any whole number from about 5 to about 100. In some embodiments x and y are, independent of one another, any whole number from about 20 to about 80. In some embodiments x and y are, independent of one another, any whole number from about 40 to about 60. In some embodiments x and y are, independent of one another, 40, 42, 44, 46, 48, 50, 52, 54, 56, 58, or 60. In one embodiment x and y are both 50. Nanoparticle cores having PLGA polymers can be further modified as needed to accommodate the attachment of a targeting agent. For example, in the instance where the targeting agent is a conjugated to a nanoparticle via the formation of a one or more ester bonds through reaction with a boronic acid present on the targeting agent and diols present on the surface of the nanoparticle, the PLGA nanoparticle may be modified to have diols on its external surface. In one embodiment, the PLGA nanoparticle core could be further modified to incorporate sugars having suitable hydroxyl groups to allow the particle to be conjugated to the boronic acid-containing targeting agent. Other such modifications could be made to facilitate the conjugation of targeting agents described herein or made apparent to those skilled in the art in view of the present disclosure.

In addition to the description of nanoparticles having cores made of cMAP and PLGA, the described nanoparticles may also be produced with a core that is made with gold, chitosan, synthetic polymers such as polyethyleneimine, dendrimers, gold, or iron oxide. Additionally, liposomes or polymeric micelles could also be used to form nanoparticles for use with the described methods. For example, a nanoparticle having a gold core could be conjugated to a targeting agent having pH sensitive linker that is bound to Tf in order to allow the gold particle to target the brain endothelial cells and cause the gold nanoparticles to be delivered to the brain parenchyma.

The described methods may be carried out using nanoparticles having cores, as described herein, that are conjugated to targeting agents to cause the nanoparticles to preferentially localize to a preferred or desired location in a subject. The described targeting agents have two main segments: a linker and a ligand. The linker includes a segment that mediates the attachment of the targeting agent to the external surface of the nanoparticle core and the ligand is a molecule that preferentially or specifically binds to a target of interest. For example, in some embodiments the targeting agent may have a polyethylene glycol (PEG) linker that is covalently bound to polymers of the nanoparticle core at one end and is attached to Tf at the other end, thereby targeting the nanoparticle to cells expressing the TfR. The described targeting agents and associated linkers can be used with a variety of the materials used to produce the nanoparticle cores described herein. In some embodiments the targeting agents and linkers may be used with a nanoparticle core made with cMAP, PLGA, gold, chitosan, synthetic polymers such as polyethyleneimine, dendrimers, gold, or iron oxide. Additionally, liposomes or polymeric micelles may also be used to form nanoparticles using the described targeting agents and linkers.

A variety of linkers may be used to carry out the described methods, and in some instances may be used with different particles. In some of the described embodiments the linker may include a polypeptide or chemical bond that can be chemically or enzymatically cleaved to cause disassociation of the ligand from the nanoparticle when the nanoparticle is inside a brain endothelial cell. For example, the linker can incorporate an enzyme target sequence just before the attached ligand to facilitate cleavage of the ligand following entry into a cellular endosome, thereby separating the ligand from the nanoparticle. In one embodiment the linker may include a cathepsin cleavage site to promote disassociation of the ligand from the nanoparticle. Those skilled in the art will understand that other sequences targeted by enzymes could be employed in a similar manner to cause disassociation of the nanoparticle from its ligand, which will allow the nanoparticle to move into the parenchyma of the CNS following excretion by the cell. Alternatively, a proteasome degradation tag could also be incorporated into the linker to cause the ligand to be degraded, but leaving the nanoparticle itself intact, as this would effectively dissociate the ligand and the nanoparticle following cellular uptake. The use of linkers with particular chemical bonds that can be chemically cleaved, such as orthoesters, acetals, ketals, imines, and hydrazones, should also be understood to be within the scope of this disclosure, as those skilled in the art will appreciate that such bonds could be used to facilitate disassociation of a ligand from a conjugated nanoparticle.

In some of the described embodiments the linker may include a disulfide bond that can be reduced to cause disassociation of the ligand from the nanoparticle when the nanoparticle is inside a brain endothelial cell. In one embodiment the disulfide bond may be placed between two component polymers bridging the nanoparticle and the ligand, such that upon reduction of the disulfide bond the nanoparticle and the ligand would be separated. In one embodiment the linker is composed of two PEG polymers that are joined by a disulfide bond where one of the PEG polymers is conjugated to the nanoparticle core and the other is conjugated to a ligand that mediates targeting when linked to the nanoparticle core. After such a particle is endocytosed by a cell, the ligand will become disassociated from the nanoparticle, which will promote egress of the nanoparticle into the parenchyma of the CNS.

In some of the described embodiments the linker may include a hydrolyzable chemical bond that can be disrupted at low pH to cause disassociation of the ligand from the nanoparticle when the nanoparticle is inside a brain endothelial cell. In one embodiment the hydrolyzable bond may be placed between two component polymers bridging the nanoparticle and the ligand, such that upon hydrolysis of the bond the nanoparticle and the ligand would be separated. In one embodiment the linker is composed of a PEG polymer conjugated to the nanoparticle core at one end and linked via a diamino ketal (DAK) to a ligand that mediates targeting. After such a particle is endocytosed by a cell, the ligand will become disassociated from the nanoparticle when it encounters a low pH environment, which will promote egress of the nanoparticle into the parenchyma of the CNS. In a particular embodiment the targeting agent having a hydrolyzable chemical bond that can be disrupted at low pH to cause disassociation of the ligand from the nanoparticle could be formed by having a ligand attached to a DAK linker that is attached to PEG-orthopyridyl disulfide (OPSS), where the ligand and OPSS are at opposite ends of the targeting agent (see, e.g., Scheme 2, below).

In some of the described embodiments the linker may include a chemical bond having a pKa that can be disrupted at low pH to cause disassociation of the ligand from the nanoparticle when the nanoparticle is inside a brain endothelial cell. In one embodiment the hydrolyzable bond may be placed at one end of the targeting agent in order to mediate conjugation to the nanoparticle core. In this configuration, a shift in the pH that favors hydrolysis of the bond between the nanoparticle core and the targeting agent would cause the core to be separated from the ligand on the targeting agent. In one embodiment the targeting agent may be a PEGylated nitrophenyl boronic acid having a ligand at the opposite end of the PEG segment and the nanoparticle core may be made with cMAP. The diols present on the cMAP and boronic acid will permit covalent bonding of the particle core and the targeting agent, but these bonds will have a pKa of approximately 6.8. Thus, once the particle is endocytosed by a cell, the ligand will become disassociated from the nanoparticle when it encounters a low pH environment, which will promote egress of the nanoparticle into the parenchyma of the CNS. In one embodiment the targeting agent described herein may have the structure of Formula VII:

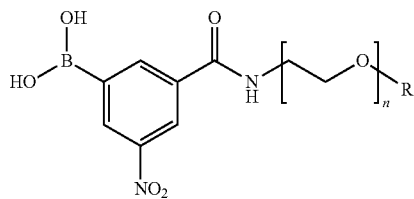

where n is any whole number between 2 and 2000, and R is a functional group including, but not limited to, a primary amine, azide, alcohol, thiol, aldehyde, or carboxylic acid. In certain embodiments, n may be any whole number between about 120 and about 180. In some embodiments, n may be any whole number between about 140 and 160. In some embodiments, n may be any one of 145, 146, 147, 148, 149, 150, 151, 152, 153, 154, 155, 156, 157, 158, 159, or 160.

Based on the forgoing disclosure those skilled in the art will understand that variant forms of linkers may be used with the described targeting agents in order to allow for delivery of the described targeted nanoparticles and then to mediate disassociation of the nanoparticle from the ligand. Such alternatives, as would be readily apparent to a skilled person in view of the present disclosure and ordinary knowledge in the art, are considered to be within the scope of this disclosure.

The described polymers, nanoparticle cores, and linkers can be combined with one or more ligands to mediate targeting of the described nanoparticles. In some embodiments the ligand will specifically bind to a receptor or surface protein expressed by a brain endothelial cell. In further embodiments the ligands specifically binds to receptor or surface protein expressed by a brain endothelial cell that undergoes transcytosis. The cellular trafficking of protein that undergo transcytosis makes them a desirable, though not absolutely necessary, target for the carrying out the methods provided herein. Targeting cellular proteins that undergo transcytosis may increase the likelihood of success of the provided methods because these cellular proteins are known to transport proteins and other molecules from one side of a cell to the other, often times in a coordinated manner. Ligands that may be used with the described methods include, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. Other cellular proteins capable of facilitating transcytosis that are known in the art may also be targeted by a ligand for carrying out the methods disclosed herein.

A variety of ligands may be used to carry out the described methods and may be used with different nanoparticles and linkers. Ligands that may be used with the described methods include, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. In some of the described embodiments the described ligands may be used in conjunction with a polypeptide or chemical bond that can be chemically or enzymatically cleaved to cause disassociation of the ligand from the nanoparticle when the nanoparticle is inside a brain endothelial cell. For example, the linker attached to the ligand can incorporate an enzyme target sequence just before the attached ligand to facilitate cleavage of the ligand following entry into a cellular endosome, thereby separating the ligand from the nanoparticle. In one embodiment the cleavage site may include a cathepsin target sequence to promote disassociation of the ligand from the nanoparticle. Those skilled in the art will understand that other sequences targeted by enzymes may be employed in a similar manner to cause disassociation of the nanoparticle from its ligand, which will allow the nanoparticle to move into the parenchyma of the CNS following excretion by the cell. Alternatively, a proteasome degradation tag could also be incorporated into the linker to cause the ligand to be degraded, but leaving the nanoparticle itself intact, as this would effectively dissociate the ligand and the nanoparticle following cellular uptake. The use of linkers with particular chemical bonds that can be chemically cleaved, such as orthoesters, acetals, ketals, imines, and hydrazones, should also be understood to be within the scope of this disclosure, as those skilled in the art will appreciate that such bonds could be used to facilitate disassociation of a ligand from a conjugated nanoparticle.

In some of the described embodiments the described ligands may be used with a linker that has a disulfide bond that can be reduced to cause disassociation of the ligand from the nanoparticle when the nanoparticle is inside a brain endothelial cell. Ligands that may be used with the described methods include, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. In one embodiment the disulfide bond may be placed between two component polymers bridging the nanoparticle and the ligand, such that upon reduction of the disulfide bond the nanoparticle and the ligand are separated. In one embodiment the linker is composed of two PEG polymers that are joined by a disulfide bond where one of the PEG polymers is conjugated to the nanoparticle core and the other is conjugated to a ligand described herein that mediates targeting when linked to the nanoparticle core. After such a particle is endocytosed by a cell, the ligand will become disassociated from the nanoparticle, which will promote egress of the nanoparticle into the parenchyma of the CNS.

In some of the described embodiments the described ligands may be associated with a linker having a hydrolyzable chemical bond that can be disrupted at low pH to cause disassociation of the ligand from the nanoparticle when the nanoparticle is inside a brain endothelial cell. Ligands that may be used with the described methods include, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. In one embodiment the hydrolyzable bond may be placed between two component polymers bridging the nanoparticle and any one of the ligands described herein, such that upon hydrolysis of the bond the nanoparticle and the ligand are separated. In one embodiment the linker is composed of a PEG polymer conjugated to the nanoparticle core at one end and linked via a diamino ketal (DAK) to any one of the described ligands at the opposite end. After such a particle is endocytosed by a cell, the ligand will become disassociated from the nanoparticle when it encounters a low pH environment, which will promote egress of the nanoparticle into the parenchyma of the CNS. In one embodiment the targeting agent having a hydrolyzable chemical bond that can be disrupted at low pH to cause disassociation of the ligand from the nanoparticle could be formed by having any one of the described ligands attached to a DAK linker that is attached to PEG-orthopyridyl disulfide (OPSS), where the ligand and OPSS are at opposite ends of the targeting agent. In a particular embodiment the targeting agent having a hydrolyzable chemical bond that can be disrupted at low pH to cause disassociation of the ligand from the nanoparticle could be formed by having Tf attached to a DAK linker that is attached to PEG-orthopyridyl disulfide (OPSS), where the ligand and OPSS are at opposite ends of the targeting agent (see, e.g., Scheme 2, below).

In some of the described embodiments the described ligands may be conjugated to a nanoparticle core by a linker that includes a chemical bond having a pKa that can be disrupted at low pH to cause disassociation of the ligand from the nanoparticle when the nanoparticle is inside a brain endothelial cell. Ligands that may be used with the described methods include, but are not limited to, transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor. In one embodiment the hydrolyzable bond may be placed at one end of the targeting agent in order to mediate conjugation to the nanoparticle core. In this configuration, a shift in the pH that favors hydrolysis of the bond between the nanoparticle core and the targeting agent would cause the core to be separated from the ligand on the targeting agent. In one embodiment the targeting agent may be a PEGylated nitrophenyl boronic acid having any one of the described ligands at the opposite end of the PEG segment. The corresponding nanoparticle core may be made with cMAP. The diols present on the cMAP and boronic acid will permit covalent bonding of the particle core and the targeting agent; however, where the bonds have a pKa of approximately 6.8 or less the targeting agent will disassociate from the nanoparticle when it encounters a low pH environment. This disassociation will promote egress of the nanoparticle into the parenchyma of the CNS. In one embodiment the targeting agent described herein may have the structure of Formula VII appended to a Tf ligand:

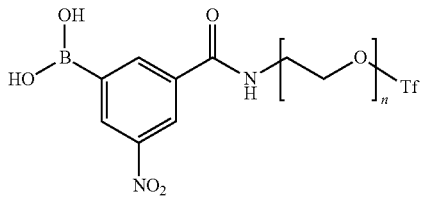

where n is any whole number between 2 and 2000. In certain embodiments, n may be any whole number between about 120 and about 180. In some embodiments, n may be any whole number between about 140 and 160. In some embodiments, n may be any one of 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, or 160. Alternatively, the PEG segment used with any of the linkers described herein may be about 2 kDa, about 5 kDa, about 6, kDa, about 7 kDa, about 8 kDa, about 9 kDa, about 10 kDa, about 11 kDa, about 12 kDa, about 13 kDa, about 14 kDa, or about 15 kDa.

Based on the forgoing disclosure those skilled in the art will understand that variant forms of linkers may be used with the described ligands to form a variety of targeting agents in order to allow for delivery of the described targeted nanoparticles and then to mediate disassociation of the nanoparticle from the ligand. Such alternatives, as would be readily apparent to a skilled person in view of the present disclosure and ordinary knowledge in the art, are considered to be within the scope of this disclosure.

To carry out the described methods it may be advantageous to control the number of targeting agents that are conjugated to the described nanoparticles. In some embodiments the described nanoparticles may have as many as 1000 conjugated targeting agents. In other embodiments the described nanoparticles may have as many as 500 conjugated targeting agents. In some embodiments the described nanoparticles may have as many as 400 conjugated targeting agents. In some embodiments the described nanoparticles may have as many as 300 conjugated targeting agents. In some embodiments the described nanoparticles may have as many as 200 conjugated targeting agents. In some embodiments the described nanoparticles may have as many as 100 conjugated targeting agents. Furthermore, the described nanoparticles may have as few as from about 20 to 50 conjugated targeting agents. In yet another embodiment the described nanoparticles may have less than 15 conjugated targeting agents. In yet another embodiment the described nanoparticles may have 10 conjugated targeting agents. In yet another embodiment the described nanoparticles may have 9 conjugated targeting agents. In yet another embodiment the described nanoparticles may have 8 conjugated targeting agents. In yet another embodiment the described nanoparticles may have 7 conjugated targeting agents. In yet another embodiment the described nanoparticles may have 6 conjugated targeting agents. In yet another embodiment the described nanoparticles may have 5 conjugated targeting agents. In yet another embodiment the described nanoparticles may have less than 4 conjugated targeting agents. In yet another embodiment the described nanoparticles may have 3 conjugated targeting agents. In yet another embodiment the described nanoparticles may have 2 conjugated targeting agents. In yet another embodiment the described nanoparticles may have 1 conjugated targeting agents. The number of targeting agents may be modulated depending on the type of nanoparticle being delivered, the delivery target, the ligand used to target the particle, or a host of other factors.

Alternatively, the nanoparticles described herein may have a mixture of targeting agents and spacing molecules (a targeting agent without an attached ligand) that are attached to the nanoparticle core. In some embodiments the number of targeting agents conjugated to a nanoparticle core will outnumber the attached spacer molecules. In some embodiments the ratio of targeting agents to spacer molecules conjugated to the core of a nanoparticle may be about 100:1, about 50:1, about 20:1, about 10:1, about 7:1, about 5:1, about 4:1, about 3:1, or about 2:1. In some embodiments the ratio of targeting agents to spacer molecules conjugated to the core of a nanoparticle may be roughly the same—about 1:1. In some embodiments the number of spacer molecules conjugated to a nanoparticle core will outnumber the attached targeting agents. In some embodiments the ratio of spacer molecules to targeting agents conjugated to the core of a nanoparticle may be about 100:1, about 50:1, about 20:1, about 10:1, about 7:1, about 5:1, about 4:1, about 3:1, or about 2:1. Another way to understand the relative distribution of spacer molecules and targeting agents conjugated to the core of a nanoparticle is in term of the percentage of total attached conjugates that are targeting agents. In some embodiments the total percentage of conjugates attached to a nanoparticle core that are targeting molecule (with the remainder being spacer molecules) is about 100%. In some embodiments the total percentage of conjugates attached to a nanoparticle core that are targeting molecule (with the remainder being spacer molecules) is about 90%. In some embodiments the total percentage of conjugates attached to a nanoparticle core that are targeting molecule (with the remainder being spacer molecules) is about 80%. In some embodiments the total percentage of conjugates attached to a nanoparticle core that are targeting molecule (with the remainder being spacer molecules) is about 70%. In some embodiments the total percentage of conjugates attached to a nanoparticle core that are targeting molecule (with the remainder being spacer molecules) is about 60%. In some embodiments the total percentage of conjugates attached to a nanoparticle core that are targeting molecule (with the remainder being spacer molecules) is about 50%. In some embodiments the total percentage of conjugates attached to a nanoparticle core that are targeting molecule (with the remainder being spacer molecules) is about 40%. In some embodiments the total percentage of conjugates attached to a nanoparticle core that are targeting molecule (with the remainder being spacer molecules) is about 30%. In some embodiments the total percentage of conjugates attached to a nanoparticle core that are targeting molecule (with the remainder being spacer molecules) is about 20%. In some embodiments the total percentage of conjugates attached to a nanoparticle core that are targeting molecule (with the remainder being spacer molecules) is about 19%. In some embodiments the total percentage of conjugates attached to a nanoparticle core that are targeting molecule (with the remainder being spacer molecules) is about 18%. In some embodiments the total percentage of conjugates attached to a nanoparticle core that are targeting molecule (with the remainder being spacer molecules) is about 17%. In some embodiments the total percentage of conjugates attached to a nanoparticle core that are targeting molecule (with the remainder being spacer molecules) is about 16%. In some embodiments the total percentage of conjugates attached to a nanoparticle core that are targeting molecule (with the remainder being spacer molecules) is about 15%. In some embodiments the total percentage of conjugates attached to a nanoparticle core that are targeting molecule (with the remainder being spacer molecules) is about 14%. In some embodiments the total percentage of conjugates attached to a nanoparticle core that are targeting molecule (with the remainder being spacer molecules) is about 13%. In some embodiments the total percentage of conjugates attached to a nanoparticle core that are targeting molecule (with the remainder being spacer molecules) is about 12%. In some embodiments the total percentage of conjugates attached to a nanoparticle core that are targeting molecule (with the remainder being spacer molecules) is about 11%. In some embodiments the total percentage of conjugates attached to a nanoparticle core that are targeting molecule (with the remainder being spacer molecules) is about 10%. In some embodiments the total percentage of conjugates attached to a nanoparticle core that are targeting molecule (with the remainder being spacer molecules) is about 9%. In some embodiments the total percentage of conjugates attached to a nanoparticle core that are targeting molecule (with the remainder being spacer molecules) is about 8%. In some embodiments the total percentage of conjugates attached to a nanoparticle core that are targeting molecule (with the remainder being spacer molecules) is about 7%. In some embodiments the total percentage of conjugates attached to a nanoparticle core that are targeting molecule (with the remainder being spacer molecules) is about 6%. In some embodiments the total percentage of conjugates attached to a nanoparticle core that are targeting molecule (with the remainder being spacer molecules) is about 5%. In some embodiments the total percentage of conjugates attached to a nanoparticle core that are targeting molecule (with the remainder being spacer molecules) is about 4%. In some embodiments the total percentage of conjugates attached to a nanoparticle core that are targeting molecule (with the remainder being spacer molecules) is about 3%. In some embodiments the total percentage of conjugates attached to a nanoparticle core that are targeting molecule (with the remainder being spacer molecules) is about 2%. In some embodiments the total percentage of conjugates attached to a nanoparticle core that are targeting molecule (with the remainder being spacer molecules) is about 1%. The ratios and percentages described herein may account for mixed populations of conjugates, such as embodiments where more than one targeting agent and/or spacer molecule is attached to a nanoparticle core.

The methods described herein rely, in part, on cellular transport of the described nanoparticles to allow localization of the particles to the brain parenchyma. In most cases the described methods will make use of some form of endosome transport through the targeted brain endothelial cell. This and other practical aspects, such as particle avidity, cause particle size to be an important factor in to consider in designing a nanoparticle for use with the provided methods. Particles suitable for use with the provided methods may be from about 40 nm to about 100 nm. In some embodiment the methods described herein may be carried out using a targeted nanoparticle that includes a nanoparticle core, as described herein, that is conjugated to any one of the targeting agents, described herein, where the total size of the targeted nanoparticle is from about 20 nm to about 100 nm. In some embodiments the size of the targeted nanoparticle is from about 40 nm to about 100 nm. In some embodiments the size of the targeted nanoparticle is from about 40 nm to about 90 nm. In some embodiments the size of the targeted nanoparticle is from about 40 nm to about 80 nm. In some embodiments the size of the targeted nanoparticle is from about 40 nm to about 70 nm. In some embodiments the size of the targeted nanoparticle is from about 40 nm to about 60 nm. In some embodiments the size of the targeted nanoparticle is from about 40 nm to about 50 nm. In some embodiments the size of the targeted nanoparticle is from about 50 nm to about 100 nm. In some embodiments the size of the targeted nanoparticle is from about 50 nm to about 90 nm. In some embodiments the size of the targeted nanoparticle is from about 60 nm to about 80 nm. In some embodiments the size of the targeted nanoparticle is from about 50 nm to about 70 nm. In some embodiments the size of the targeted nanoparticle is from about 70 nm to about 100 nm.

The methods described herein rely, in part, on cellular transport of the described nanoparticles to allow localization of the particles to the brain parenchyma. In designing nanoparticles to cross the brain endothelial cells of the blood-brain barrier, it is important to take into consideration aspects of the particles that may facilitate, rather than inhibit, the interaction of the particles with these endothelial cells. One such property is the charge of the particle. Accordingly, the methods described may be carried out using a targeted nanoparticle that includes a nanoparticle core, as described herein, that is conjugated to any one of the targeting agents, described herein, where the charge of the targeted nanoparticle is near neutral. Zeta potential of the described particles can vary depending on the materials used to make the particle core, the linker used, and the ligand. In most cases, the zeta potential of the targeted nanoparticle will fall in the negative range. Zeta potential of the nanoparticles for use with the methods described herein can range from about −0.5 mV to about −15.0 mV. In some embodiments the described nanoparticle will have a zeta potential of from about −2.0 mV to about −11.0 mV. In some embodiments the described nanoparticle will have a zeta potential of from about −3.0 mV to about −11.0 mV. In some embodiments the described nanoparticle will have a zeta potential of from about −4.0 mV to about −11.0 mV. In some embodiments the described nanoparticle will have a zeta potential of from about −5.0 mV to about −11.0 mV. In some embodiments the described nanoparticle will have a zeta potential of from about −6.0 mV to about −11.0 mV. In some embodiments the described nanoparticle will have a zeta potential of from about −7.0 mV to about −11.0 mV. In some embodiments the described nanoparticle will have a zeta potential of from about −8.0 mV to about −11.0 mV. In some embodiments the described nanoparticle will have a zeta potential of from about −9.0 mV to about −11.0 mV. In some embodiments the described nanoparticle will have a zeta potential of from about −2.0 mV to about −10.0 mV. In some embodiments the described nanoparticle will have a zeta potential of from about −2.0 mV to about −9.0 mV. In some embodiments the described nanoparticle will have a zeta potential of from about −2.0 mV to about −8.0 mV. In some embodiments the described nanoparticle will have a zeta potential of from about −2.0 mV to about −7.0 mV. In some embodiments the described nanoparticle will have a zeta potential of from about −4.0 mV to about −8.0 mV. In some embodiments the described nanoparticle will have a zeta potential of from about −5.0 mV to about −7.0 mV. In some embodiments the described nanoparticle will have a zeta potential of −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2, −7.3, −7.4, −7.5, −7.6, −7.7, −7.8, −7.9, or −8.0 mV.

The described method may be used to deliver therapeutic or imaging agents to the brain of a subject, by loading the described nanoparticles with a therapeutic agent or imaging agent of interest prior to administration of the nanoparticle to the subject. Following delivery of the loaded nanoparticle, the targeting agent will facilitate delivery to a target cell of interest, such as a brain endothelial cell. Following internalization by the target cell, the nanoparticle will dissociate from the targeting agent. In the case of brain endothelial cells, the internalized nanoparticle will then be excreted from the cell into the interstitial space of the brain where the particle will destabilize and secrete the loaded agent, thereby delivering the agent to the brain or other target location. In some embodiments the described methods may be carried out to deliver a neurotransmitter such as serotonin or dopamine to the brain, which may be used to treat a neurological disorder. Other agents for use in treating neurological disorders may also be delivered to the brain via the described methods. Imaging agents that might not readily access the brain on their own may also be delivered using the described methods. In some embodiments the described methods may be used to deliver a nanoparticle carrying the imaging agent Cu64 to the brain of a subject to allow for imaging. Further, the described methods may be used to deliver a combination of one or more therapeutic agents, imaging agents, or both therapeutic agents, imaging agent to the brain of a subject.

The nanoparticles described herein may be administered orally in any acceptable dosage form such as capsules, tablets, aqueous suspensions, solutions or the like. The nanoparticles may also be administered parenterally including but not limited to: subcutaneous, intravenous, intramuscular, intra-articular, intra-synovial, intrasternal, and intracranial injection or infusion techniques. Alternatively, the nanoparticles will be administered intravenously or intraperitoneally, for example, by injection.

The subject may be any animal, and preferably is a mammal such as a mouse, rat, hamster, guinea pig, rabbit, cat, dog, monkey, donkey, cow, horse, pig, and the like. Most preferably, the mammal is a human. In some embodiments, subjects may be administered at least one of the described nanoparticles in a daily dose range of 0.01 µg to 500 mg per kg of the weight of the subject. The dose administered to the subject may also be measured in terms of total amount of at least one of the described nanoparticles administered per day. In some embodiments, a subject is administered 5 to 5000 milligrams of at least one of the described nanoparticles per dose. In some embodiments, a subject is administered up to 10 milligrams of at least one of the described nanoparticles per dose. In some embodiments, a subject is administered up to 100 milligrams of at least one of the described nanoparticles per dose. In some embodiments, a subject is administered up to 250 milligrams of at least one of the described nanoparticles per dose. In some embodiments, a subject is administered up to 500 milligrams of at least one of the described nanoparticles per dose. In some embodiments, a subject is administered up to 750 milligrams of at least one of the described nanoparticles per dose. In some embodiments, a subject is administered up to 1000 milligrams of at least one of the described nanoparticles per dose. In some embodiments, a subject is administered up to 1500 milligrams of at least one of the described nanoparticles per dose. In some embodiments, a subject is administered up to 2000 milligrams of at least one of the described nanoparticles per dose. In some embodiments, a subject is administered up to 2500 milligrams of at least one of the described nanoparticles per dose. In some embodiments, a subject is administered up to 3000 milligrams of at least one of the described nanoparticles per dose. In some embodiments, a subject is administered up to 3500 milligrams of at least one of the described nanoparticles per dose. In some embodiments, a subject is administered up to 4000 milligrams of at least one of the described nanoparticles per dose. In some embodiments, a subject is administered up to 4500 milligrams of at least one of the described nanoparticles per dose. In some embodiments, a subject is administered up to 5000 milligrams of at least one of the described nanoparticles per dose. In some embodiments, the described methods may be carried out so the nanoparticles described herein is administered to a subject weekly, bi-weekly, monthly, bi-month, semi-annually, or annually. Treatment may be initiated with smaller dosages that are less than the optimum dose followed by an increase in dosage over the course of the treatment until the optimum effect under the circumstances is reached.

The methods provided herein may be carried out by administering to a subject the nanoparticles described herein while suspended in a pharmaceutically acceptable carrier. Such compositions are useful, for example, for administration to patients to treat neurological disorders. The compositions may be formulated as any of various preparations that are known and suitable in the art. In some embodiments, the compositions are aqueous formulations. Aqueous solutions may be prepared by admixing the nanoparticles in water or suitable physiologic buffer, and optionally adding suitable colorants, preservatives, stabilizing and thickening agents and the like as desired. Aqueous suspensions may also be made by dispersing the nanoparticles in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid preparations. Such liquids include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions may be formulated for injection into a subject. For injection, the compositions described may be formulated in aqueous solutions such as water or alcohol, or in physiologically compatible buffers such as Hanks's solution, Ringer's solution, or physiological saline buffer. The solution may contain one or more formulatory agents such as suspending, stabilizing or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

Described herein are kits for producing a nanoparticle targeted for delivery to the brain. For example, the described kits may contain the materials and reagents to assemble nanoparticles having an exterior surface of cationic mucic acid polymers (cMAP), poly(lactic-co-glycolic acid) (PLGA), chitosan, synthetic polymers such as polyethyleneimine, gold, iron oxide, or other analogous material as understood by those skilled in the art; a targeting agent specific for a receptor expressed by brain endothelial cells, wherein the targeting agent includes a ligand that is conjugated to a linker that causes disassociation of the ligand from the nanoparticle when inside a brain endothelial cell; and instructions for assembling the nanoparticle. The described kits may also include a ligand for targeting brain endothelial cell proteins known to undergo transcytosis.

Also described herein are kits for producing a nanoparticle targeted for delivery to the brain. For example, the described kits may contain the materials and reagents to assemble nanoparticles having an exterior surface of cationic mucic acid polymers (cMAP), poly(lactic-co-glycolic acid) (PLGA), chitosan, synthetic polymers such as polyethyleneimine, gold, iron oxide, or other analogous material as understood by those skilled in the art; a targeting agent specific for a receptor expressed by brain endothelial cells, wherein the targeting agent includes a ligand that is conjugated to a linker that causes disassociation of the ligand from the nanoparticle when inside a brain endothelial cell; and instructions for assembling the nanoparticle. The described kits may also include a ligand for targeting brain endothelial cell, such as transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor.

Provided below are illustrative embodiments of the subject matter previously described. These embodiments are meant to illustrate, not to limit, the foregoing disclosure.

1. A method of delivering a nanoparticle to the brain of a subject comprising administering to the subject a nanoparticle having a nanoparticle core and a targeting agent, wherein said targeting agent includes a ligand specific for a receptor expressed by brain endothelial cells and a linker that connects the ligand to the nanoparticle core, wherein said linker causes dissociation of the ligand from the nanoparticle when inside a brain endothelial cell, and wherein said ligand is conjugated to the external surface of the nanoparticle core through the linker.

2. The method of embodiment 1, wherein:
   the surface of the nanoparticle core comprises any one of cationic mucic acid polymers (cMAP), poly(lactic-co-glycolic acid) (PLGA), chitosan, synthetic polymers such as polyethyleneimine, dendrimers, gold, or iron oxide;
   the ligand is any one of transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor; and
   the linker comprises a nitrophenyl boronic acid when unbound to the nanoparticle and a forms a nitrophenyl boronic ester when bound to the nanoparticle.

3. The method of embodiment 2, wherein the nanoparticle core comprises cationic mucic acid polymer (cMAP) having the structure:

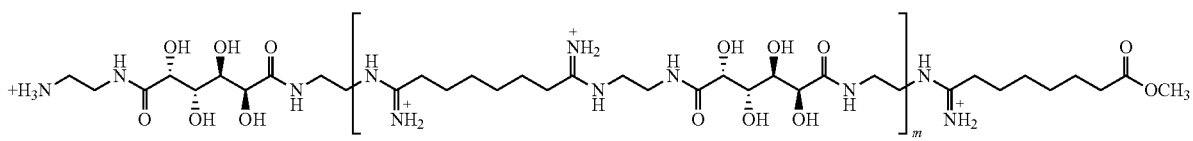

wherein m is any whole number between 5 and 50.

4. The method of embodiment 3, wherein m is any one of 6, 7, 8, 9, 10, 11, 12, 13, 14, 15, or 16.

5. The method of any one previous embodiment, wherein the linker of the targeting agent further comprises a polyethylene glycol (PEG) polymer between said nitrophenyl boronic acid and said ligand.

6. The method of embodiment 5, wherein the linker has the structure:

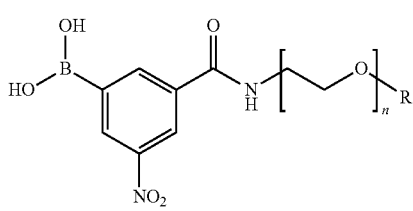

where n is any whole number between 2 and 2000 and R is a functional group selected from a primary amine, azide, alcohol, thiol, aldehyde, or carboxylic acid.

7. The method of any one previous embodiment wherein the targeting agent is

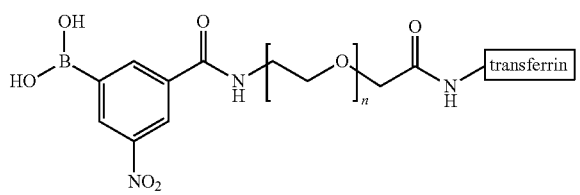

and n is any whole number between 2 and 2000.

8. The method of embodiment 6 or 7, wherein n is any whole number from about 110 to about 150.

9. The method of embodiment 1, wherein:
the surface of the nanoparticle core comprises poly(lactic-co-glycolic acid) (PLGA) polymers,
the ligand is any one of transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor; and
the linker comprises a PEG polymer.

10. The method of embodiment 9, wherein the PEG polymer is conjugated to the ligand via a disulfide bond or a polypeptide having an enzyme cleavage site.

11. The method of embodiment 9 or 10, wherein the nanoparticle core comprises PLGA having the structure:

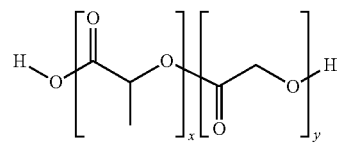

wherein x and y are independently any whole number between 5 and 500.

12. The method of embodiment 11, wherein x and y are independently any one of 40, 45, 50, 55, or 60.

13. The method of embodiment 11 or 12, wherein the nanoparticle core comprising PLGA is conjugated to a PEG linker and has the structure:

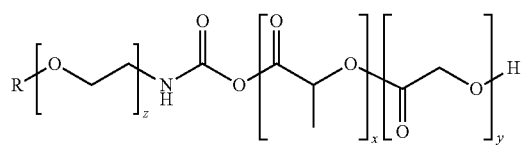

and z is any whole number between 2 and 2000 and x and y are independently any whole number between 5 and 500, and R is selected from a primary amine, azide, alcohol, thiol, aldehyde, or carboxylic acid.

14. The method of embodiment 13, wherein z is any whole number from about 110 to about 150 and x and y are 50.

15. The method of any one of embodiments 9 to 14, wherein the targeting agent is

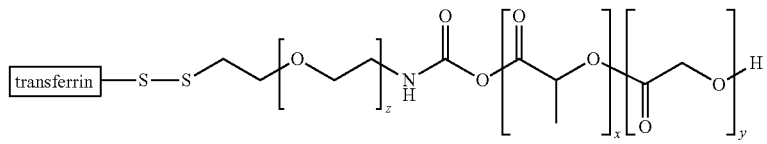

and z is any whole number from about 110 to about 150 and x and y are 50.

16. The method of embodiment 1, wherein:
the surface of the nanoparticle core comprises any one of cationic mucic acid polymers (cMAP), poly(lactic-co-glycolic acid) (PLGA), chitosan, synthetic polymers such as polyethyleneimine, dendrimers, gold, or iron oxide;
the ligand is any one of transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor; and the linker comprises a diamino ketal conjugated to PEG.

17. The method of embodiment 1, wherein the linker includes a disulfide bond that can be reduced to cause dissociation of the ligand from the nanoparticle when the nanoparticle is inside a brain endothelial cell.

18. The method of embodiment 1, wherein the linker includes a polypeptide or chemical bond that can be enzymatically cleaved to cause dissociation of the ligand from the nanoparticle when the nanoparticle is inside a brain endothelial cell.

19. The method of embodiment 1, wherein the linker includes a hydrolyzable chemical bond that can be disrupted at low pH to cause dissociation of the ligand from the nanoparticle when the nanoparticle is inside a brain endothelial cell.

20. The method of embodiment 1, wherein the linker includes a chemical bond having a pKa that can be disrupted at low pH to cause dissociation of the ligand from the nanoparticle when the nanoparticle is inside a brain endothelial cell.

21. The method of embodiment 19 or 20, wherein low pH is a value from about 6.8 to about 2.0.

22. The method of embodiment 21, wherein low pH is a value from about 5.5 to about 2.5.

23. The method of embodiment 21, wherein low pH is a value from about 5.5 to about 4.0.

24. The method of any one of embodiments 17 to 23, wherein the surface of the nanoparticle core comprises poly(lactic-co-glycolic acid) (PLGA).

25. The method of any one of embodiments 17 to 23, wherein the surface of the nanoparticle core comprises cationic mucic acid polymers (cMAP).

26. The method of any one of embodiments 17 to 23, wherein the surface of the nanoparticle core comprises gold.

27. The method of embodiment 1, wherein:
the surface of the nanoparticle core comprises the surface of the nanoparticle core comprises any one of cationic mucic acid polymers (cMAP), poly(lactic-co-glycolic acid) (PLGA), chitosan, synthetic polymers such as polyethyleneimine, dendrimers, gold, or iron oxide;
the ligand is any one of transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor; and
the linker comprises an acid-cleavable chemical bond selected from an orthoester, acetal, ketal, imine, or hydrazone, that is conjugated to PEG.

28. The method of any one previous embodiment, wherein the nanoparticle comprises less than 200 targeting agents conjugated to its surface.

29. The method of any one previous embodiment, wherein the nanoparticle comprises less than 20 targeting agents conjugated to its surface.

30. The method of any one previous embodiment, wherein the nanoparticle comprises less than 5 targeting agents conjugated to its surface.

31. The method of any one previous embodiment, wherein the nanoparticle comprises a single targeting agent conjugated to its surface.

32. The method of any one previous embodiment, wherein the nanoparticle has a size of from about 40 nm to about 100 nm as measured by dynamic light scattering (DLS).

33. The method of embodiment 32, wherein the nanoparticle has a size of from about 50 nm to about 70 nm as measured by dynamic light scattering (DLS).

34. The method of embodiments 33, wherein the nanoparticle has a size of 55 nm, 56 nm, 57 nm, 58 nm, 59 nm, 60 nm, 61 nm, 62 nm, 63 nm, 64 nm, 65 nm, 66 nm, 67 nm, 68 nm, or 69 nm as measured by dynamic light scattering (DLS).

35. The method of any one previous embodiment, wherein the nanoparticle has an average zeta potential of from about −0.5 mV to about −15.0 mV as measured by phase analysis light scattering.

36. The method of embodiment 35, wherein the nanoparticle has an average zeta potential of −5.0, −5.1, −5.2, −5.3, −5.4, −5.5, −5.6, −5.7, −5.8, −5.9, −6.0, −6.1, −6.2, −6.3, −6.4, −6.5, −6.6, −6.7, −6.8, −6.9, −7.0, −7.1, −7.2, −7.3, −7.4, −7.5, −7.6, −7.7, −7.8, −7.9, or −8.0 mV as measured by phase analysis light scattering.

37. The method of any one previous embodiment, wherein the nanoparticle further comprises a therapeutic agent.

38. The method of embodiment 37, wherein the therapeutic agent is effective against a neurological disorder.

39. The method of embodiment 37 or 38, wherein the therapeutic agent is serotonin or dopamine.

40. The method of any one previous embodiment, wherein the nanoparticle further comprises an imaging agent.

41. The method of embodiment 40, wherein the imaging agent is Cu-64.

42. The method of any one previous embodiment, wherein the nanoparticle includes a first targeting agent and a second targeting agent, wherein the second targeting agent comprises:
a linker that is not amenable to disassociation from the nanoparticle core when inside of a brain endothelial cell, and
a ligand that targets the particle to a specific cell in the brain.

43. A kit for producing a nanoparticle targeted for delivery to the brain comprising cationic mucic acid polymers (cMAP); a targeting agent specific for a receptor expressed by brain endothelial cells, wherein said targeting agent includes a ligand that is conjugated to a linker that causes dissociation of the ligand from the nanoparticle when inside a brain endothelial cell; and instructions for assembling the nanoparticle.

44. A kit for producing a nanoparticle targeted for delivery to the brain comprising poly(lactic-co-glycolic acid) (PLGA); a targeting agent specific for a receptor expressed by brain endothelial cells, wherein said targeting agent includes a ligand that is conjugated to a linker that causes dissociation of the ligand from the nanoparticle when inside a brain endothelial cell; and instructions for assembling the nanoparticle.

45. The kit of embodiment 35 or 36, wherein the ligand is any one of transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor; and wherein the linker comprises a nitrophenyl boronic acid when unbound to the nanoparticle and a forms a nitrophenyl boronic ester when bound to the nanoparticle.

46. The kit of any one of embodiments 43 to 45, further comprising a therapeutic agent or an imaging agent.

The following examples are provided to describe the embodiments described herein with greater detail. They are intended to illustrate, not to limit, the embodiments.

Figure 3:
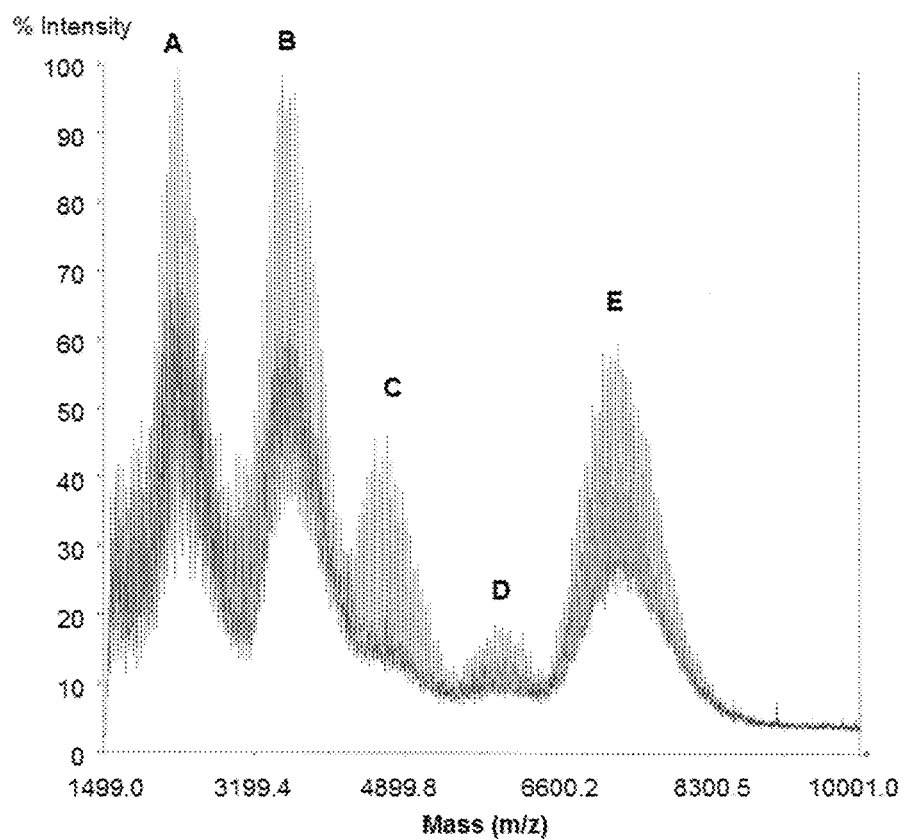
FIG. 3. MALDI-TOF analysis of PEG coupling reaction. MALDI spectra of $NH_2$-PEG-SH (3.4 kDa) and COOH-PEG-SH (2 kDa) reaction at 24 hours. Peaks A and B correspond to the reactants, COOH-PEG-SH and $NH_2$-PEG-SH, respectively. Peaks C, D, and E correspond to the three potential products as outlined in Scheme 1, the 4 kDa, 5.4 kDa and 6.8 kDa polymers, respectively.
Figure 4:
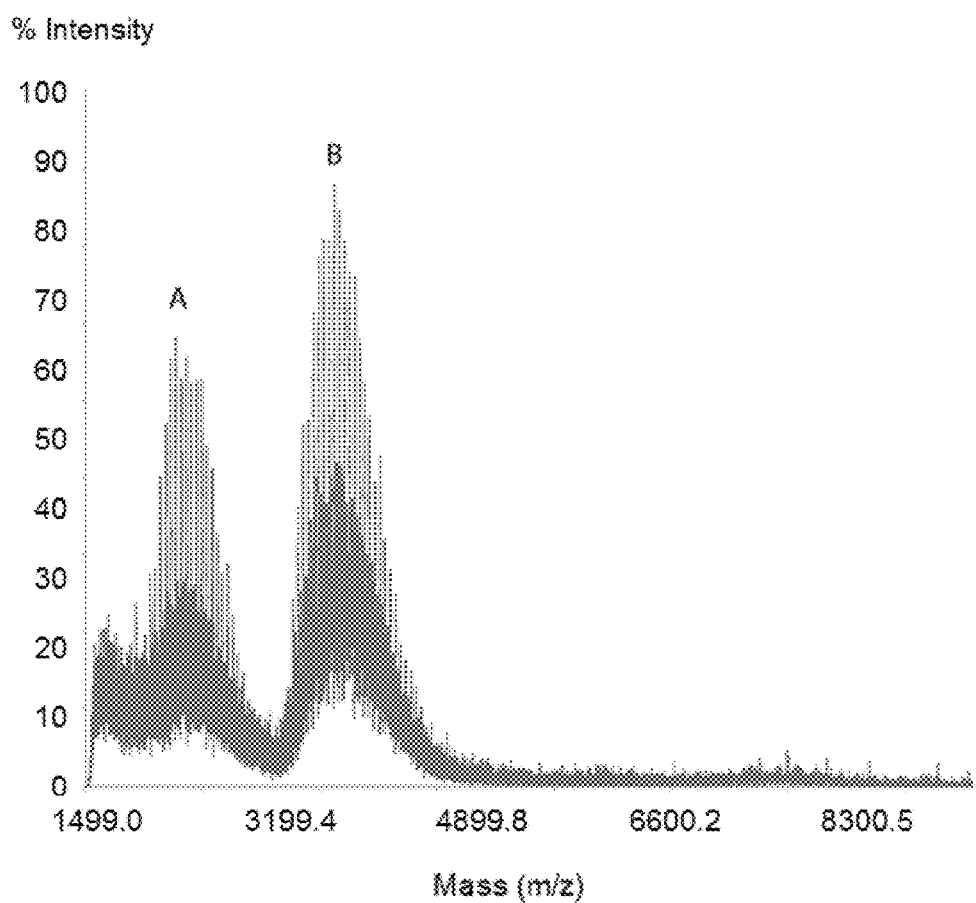
FIG. 4. MALDI-TOF analysis of disulfide cleavage reaction. MALDI spectra of $NH_2$-PEG-SH (3.4 kDa) and COOH-PEG-SH (2 kDa) reaction after addition of excess beta-mercaptoethanol (BME). Peaks A and B correspond to the parent polymers, COOH-PEG-SH and $NH_2$-PEG-SH, respectively. There is no evidence of products from disulfide bond formation between PEG polymers due to thiol-disulfide exchange caused by the excess BME.

Example I—Disassociation of a Ligand from a Nanoparticle Using a Reduction-Sensitive Linker Studies were conducted to assess whether a nanoparticle with a conjugated targeting agent could be disassociated from the ligand of the targeting agent using a reduction-sensitive linker. An initial study was conducted to determine whether disulfide linked polymers could be separated to yield the original polymers. For this work poly(lactic-co-glycolic acid)-polyethylene glycol (PLGA-PEG) molecules were synthesized to contain disulfide bonds near the center of the PEG molecule through an oxidation reaction of two PEG molecules containing terminal thiol groups (Scheme 1). Matrix-assisted laser desorption/ionization time-of-flight mass spectrometry (MALDI-TOF) was employed to confirm the oxidation reaction proceeded (FIG. 3). Reducing agent, beta-mercaptoethanol (BME) was then added to the disulfide-linked PEG polymers, and MALDI-TOF confirmed the disulfide bond was reduced and the two parent polymers were regenerated (FIG. 4).

Scheme 1. Formation of disulfide bond between two PEG polymers. Polymer molecular weights are written beneath the appropriate reactant or product.

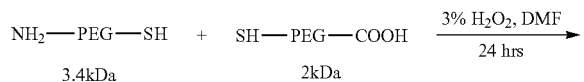

$NH_2$—PEG—SH + SH—PEG—COOH $\xrightarrow{3\% H_2O_2, DMF}{24 hrs}$ 3.4kDa  2kDa -continued $NH_2$—PEG—S—S—PEG—COOH 5.4kDa

+

$NH_2$—PEG—S—S—PEG—$NH_2$ 6.8kDa

+

COOH—PEG—S—S—PEG—COOH

4kDa

Figure 5:
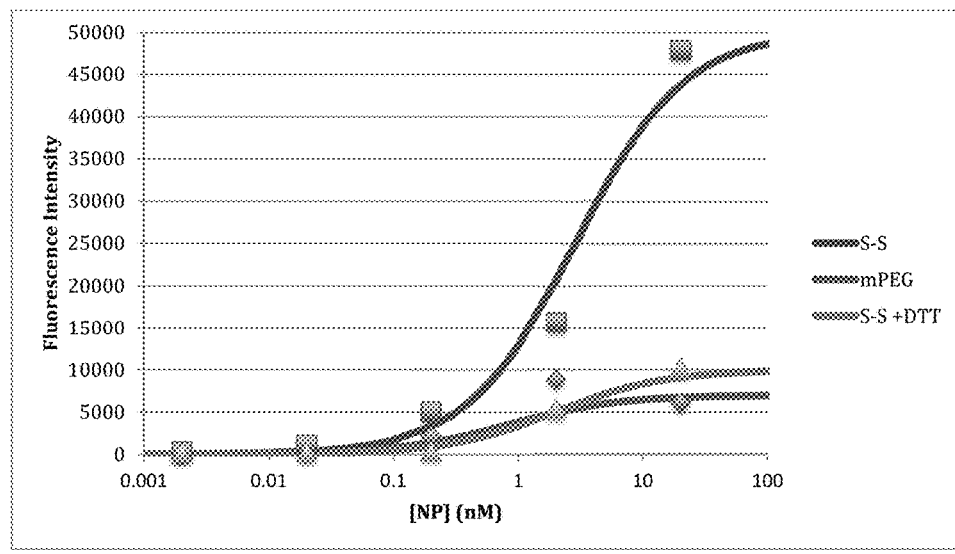
FIG. 5. Disulfide-containing nanoparticle binding avidity to Neuro2A cells. Measured data points are indicated by squares, diamonds or triangles for the disulfide-containing PLGA-PEG-Tf nanoparticles (S—S), disulfide-containing PLGA-PEG-Tf nanoparticles after treatment with dithiothreitol (S—S+DTT) and methoxy-terminated PLGA-PEG nanoparticles (mPEG), respectively. The model curves for each formulation are based on the Langmuir binding isotherm.

Having determined that disulfide-linked polymers can be reduced to yield the original component polymers, studies were conducted to determine whether this same principle could be used to dissociate a ligand bound to a targeting nanoparticle. To assess this, Neuro2A cells that express TfR were incubated with varying concentrations of methoxy-terminated poly(lactic-co-glycolic) acid polyethylene glycol particles (PLGA-mPEG), disulfide-containing PLGA-PEG-Tf (PLGA-PEG-S—S-PEG-Tf), or disulfide containing PLGA-PEG-Tf after treatment with reducing agent, dithiothreitol (DTT). The binding curves of each of these formulations are presented in FIG. 5. Nanoparticle sizes and zeta potentials of each formulation are listed in Table 1.

TABLE 1

| Formulation | Diameter (nm) | Zeta potential (mV) |
|---|---|---|
| mPEG | 56.6 | −6.6 ± 2.6 |
| Low-Tf | 58.7 | −5.8 ± 3.8 |
| High-Tf | 56.2 | −8.5 ± 1.6 |
| High-Tf + S-S | 65.6 | −5.9 ± 3.0 |
| High-Tf + S-S + DTT | 65.6 | −5.9 ± 3.0 |

The Tf targeted, disulfide-containing nanoparticles bound the most to Neuro2A cells and have the highest avidities for the TfRs. Cleavage of the disulfide bond by treatment with DTT and subsequent disassociation of Tf from the nanoparticle significantly lowers the nanoparticles' binding to the Neuro2A cells, seen by the decreased maximal fluorescence intensity. Non-targeted (PLGA-mPEG) nanoparticles have essentially the same binding curves as the DTT-treated nanoparticles that suggests most of the binding by the DTT-treated particles is due to non-specific interaction of nanoparticles with the cell surface. These results demonstrate that the disulfide-containing nanoparticles bind with high avidity to TfRs but once Tf falls off the nanoparticles, they bind non-specifically to the Neuro2A cells just as the non-targeted nanoparticles. This indicates that a disulfide bond is present in the nanoparticle and when cleaved, causes loss of the targeting ligand from the nanoparticle and subsequent loss of binding avidity for the targeting ligand's receptor.

Figure 6:
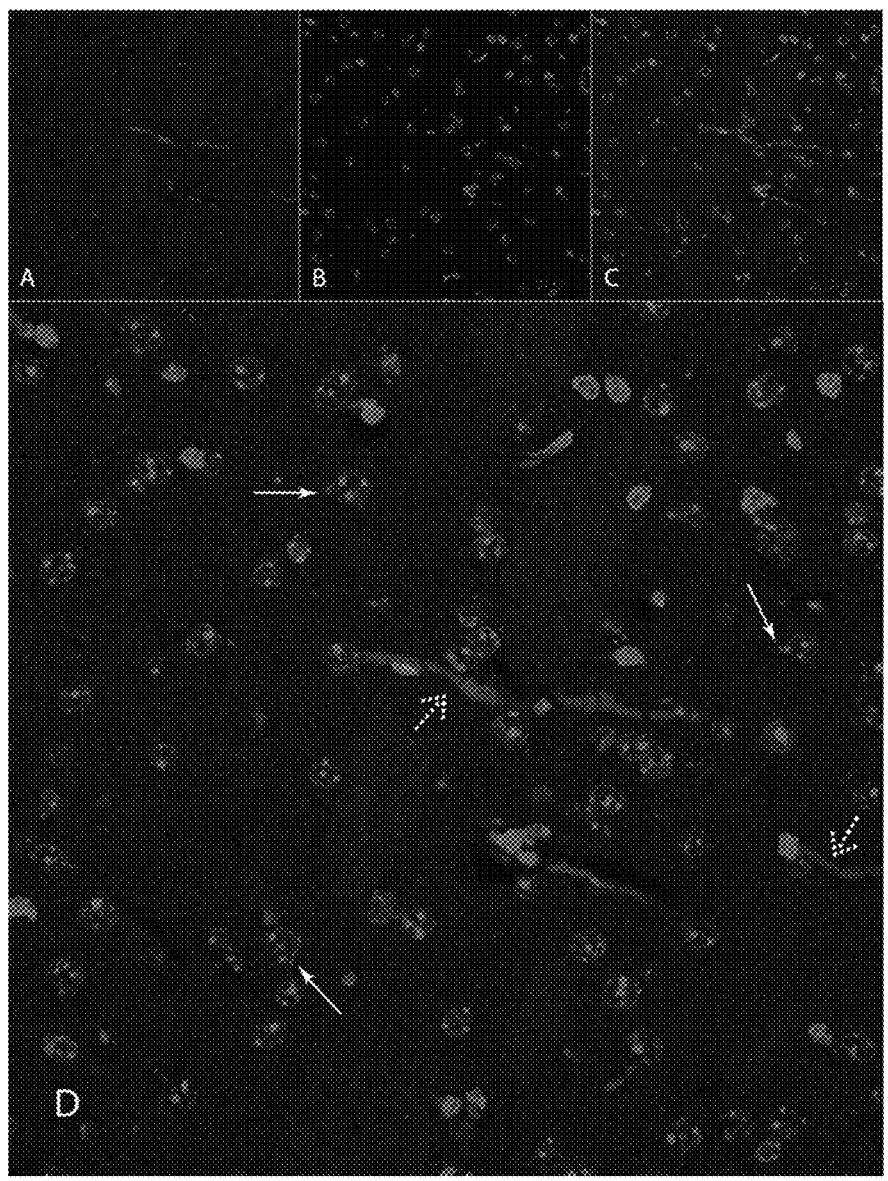
FIG. 6. Confocal images of PLGA-mPEG nanoparticles in mouse brain sections. Panel A: 488 nm excitation, panel B: DAPI signal, panel C: merged image of Panels A and B. Panel D shows an enlarged view of the merged image in Panel C. Solid arrows indicate fluorescence co-localized with cell nuclei. Since this phenomenon was seen with non-targeted particles, it was considered normal tissue background fluorescence. Dotted arrows indicate blood vessels.
Figure 7:
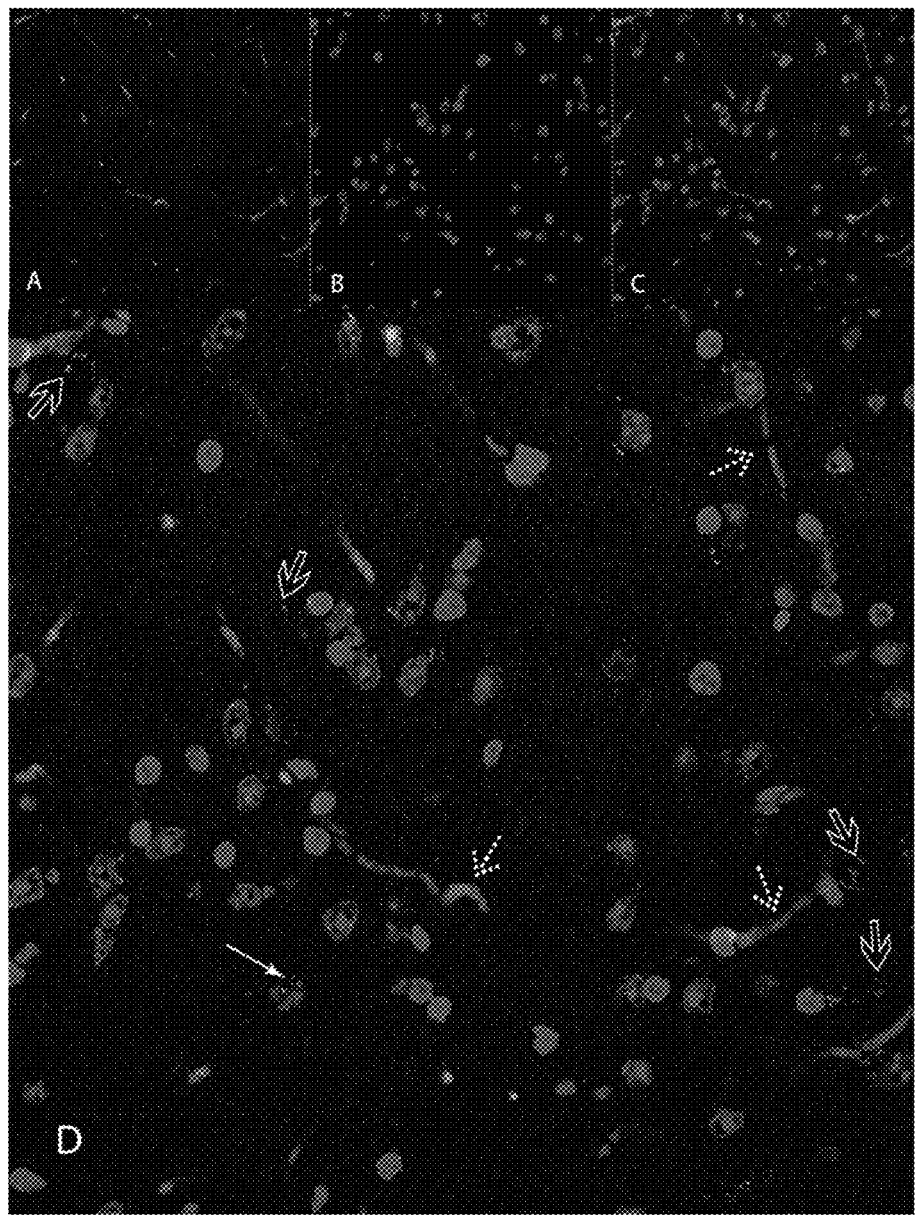
FIG. 7. Confocal images of low-Tf PLGA-PEG nanoparticles in mouse brain sections. Panel A shows fluorescence from 488 nm excitation. Panel B shows the DAPI signal. Panel C shows a merged image of Panels A and B. Panel D shows an enlarged view of the merged image in Panel C. Solid white arrows indicate fluorescence co-localized with cell nuclei. Dotted white arrows indicate blood vessels. Hollow white arrows indicate fluorescence in the parenchyma not associated with cell nuclei determined to be nanoparticle signal.
Figure 8:
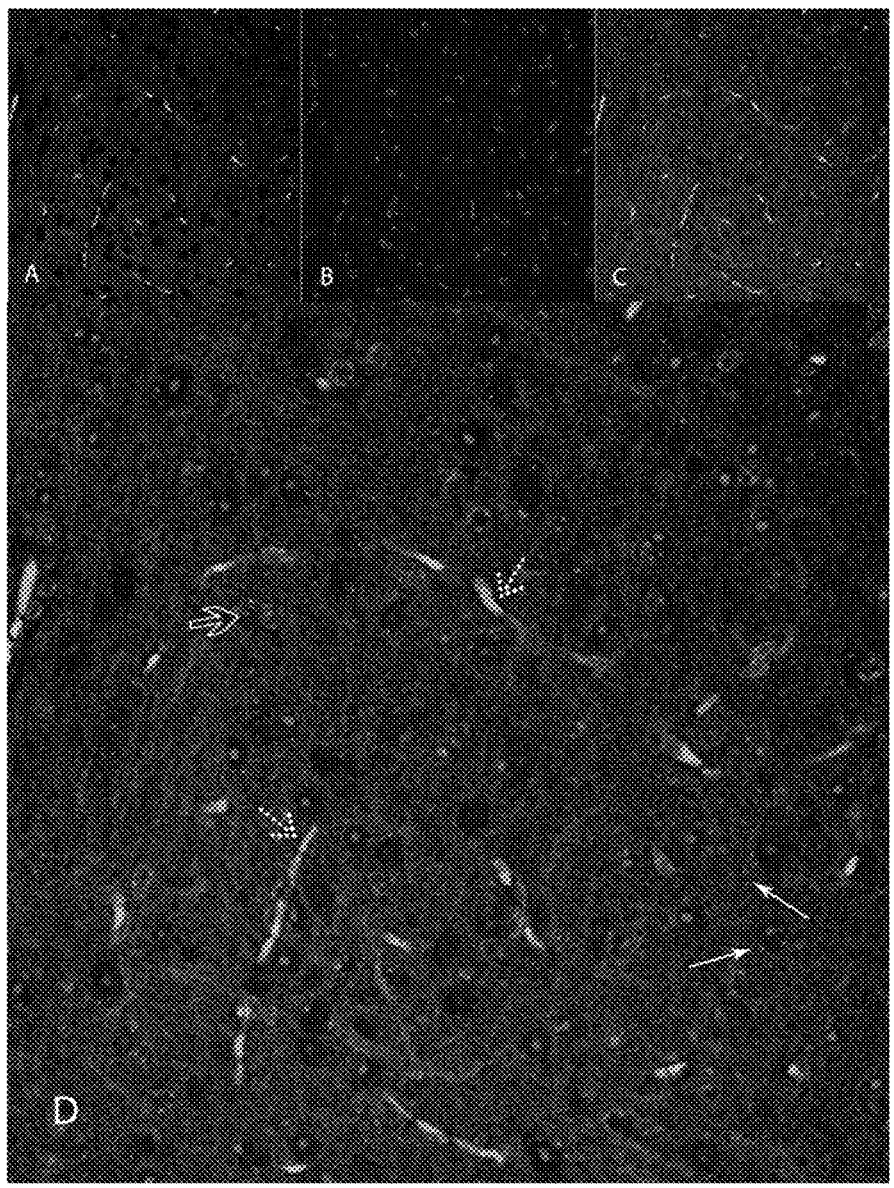
FIG. 8. Confocal images of high-Tf PLGA-PEG nanoparticles in mouse brain sections. Panel A shows fluorescence from 488 nm excitation. Panel B shows the DAPI signal. Panel C shows a merged image of Panels A and B. Panel D shows an enlarged view of the merged image in Panel C. Solid white arrows indicate fluorescence co-localized with cell nuclei. Dotted white arrows indicate blood vessels. Hollow white arrows indicate fluorescence in the parenchyma not associated with cell nuclei determined to be nanoparticle signal.
Figure 9:
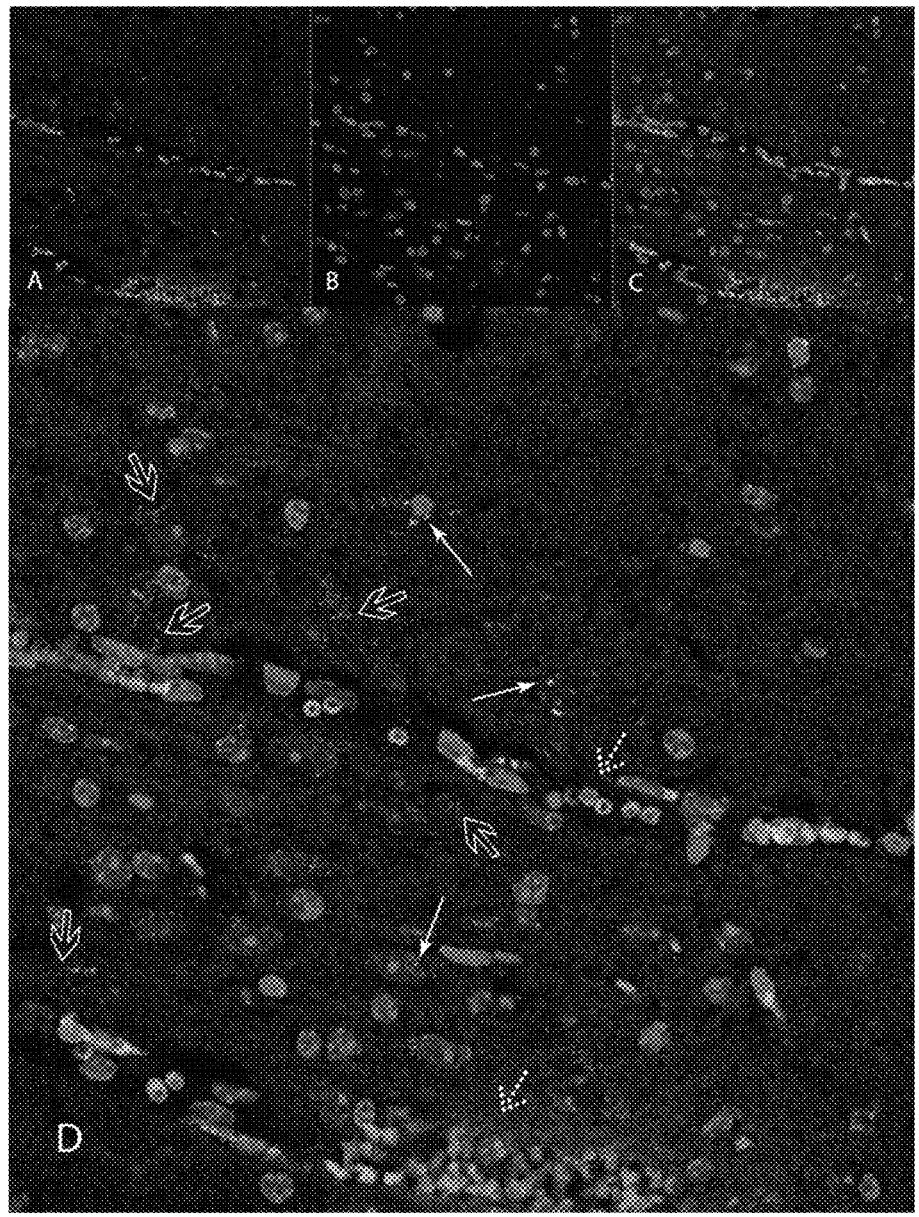
FIG. 9. Confocal images of high-Tf plus disulfide PLGA-PEG nanoparticle in mouse brain sections. Panel A shows fluorescence from 488 nm excitation. Panel B shows the DAPI signal. Panel C shows a merged image of Panels A and B. Panel D shows an enlarged view of the merged image in Panel C. Solid white arrows indicate fluorescence co-localized with cell nuclei. Dotted white arrows indicate blood vessels. Hollow white arrows indicate fluorescence in the parenchyma not associated with cell nuclei determined to be nanoparticle signal.

Studies were conducted to determine whether nanoparticles with targeting agents having a dissociable ligand showed improved ability to cross the blood-brain barrier. BALB/c mice were administered, via lateral tail vein injection, four fluorescently-labeled PLGA nanoparticle formulations: (1) non-targeted nanoparticles (mPEG); (2) low avidity nanoparticles (30 Tf per nanoparticle); (3) high avidity nanoparticles (300 Tf per nanoparticle), and (4) a high avidity nanoparticle containing a disulfide linker (300 Tf per nanoparticle+S—S). FIGS. 6-9 illustrate to what extent each nanoparticle formulation was observed to reach the brain parenchyma. Nanoparticles were positively identified as distinct fluorescent signal above autofluorescence, clearly away from the blood vessels and in the parenchyma. Fluorescence associated with cell nuclei was seen in the negative controls and was therefore not considered to be specific to nanoparticles. Untargeted PLGA-mPEG nanoparticles did not access the brain parenchyma and remained exclusively in the vasculature (FIG. 6). Low-Tf PLGA-PEG nanoparticles were present in the parenchyma, consistent with the observations of others (FIG. 7). High-Tf PLGA-PEG nanoparticles were not clearly seen in the brain parenchyma, with a similar fluorescent pattern to the PLGA-mPEG formulation (FIG. 8). This is consistent with the necessity for the nanoparticles' avidity to be tuned for successful release into the brain parenchyma. High-Tf+S—S nanoparticles provided the greatest amount of fluorescence within the brain parenchyma (FIG. 9).

Example II—Nanoparticles Having a pH-Sensitive Linker

Disassociation of a Ligand from a Nanoparticle Using a pH-Sensitive Linker

Figure 10:
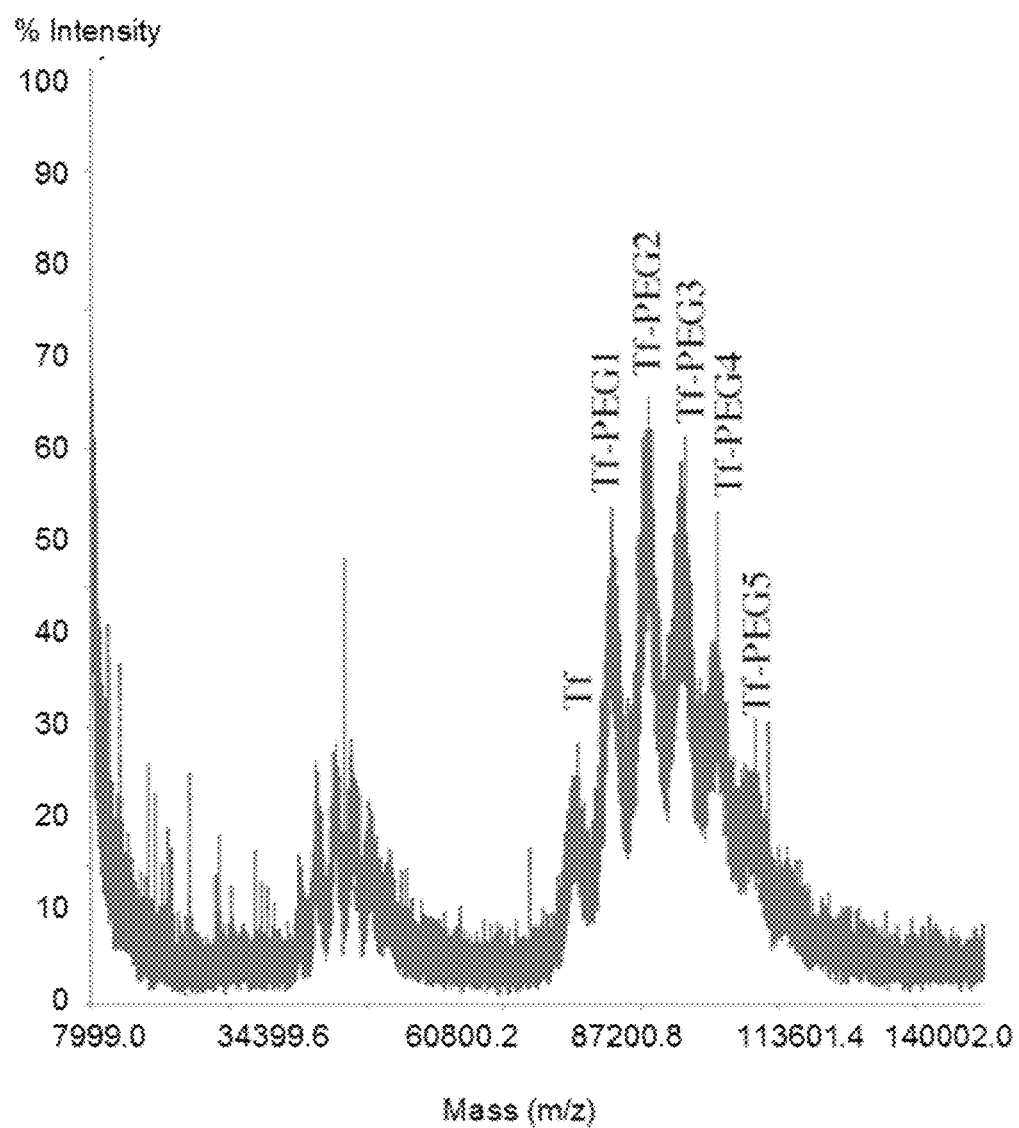
FIG. 10. MALDI-TOF trace of conjugation reaction of DSS-DAK-PEG-OPSS to Tf. Unreacted Tf and several orders of PEGylated-Tf are labeled.
Figure 11A:
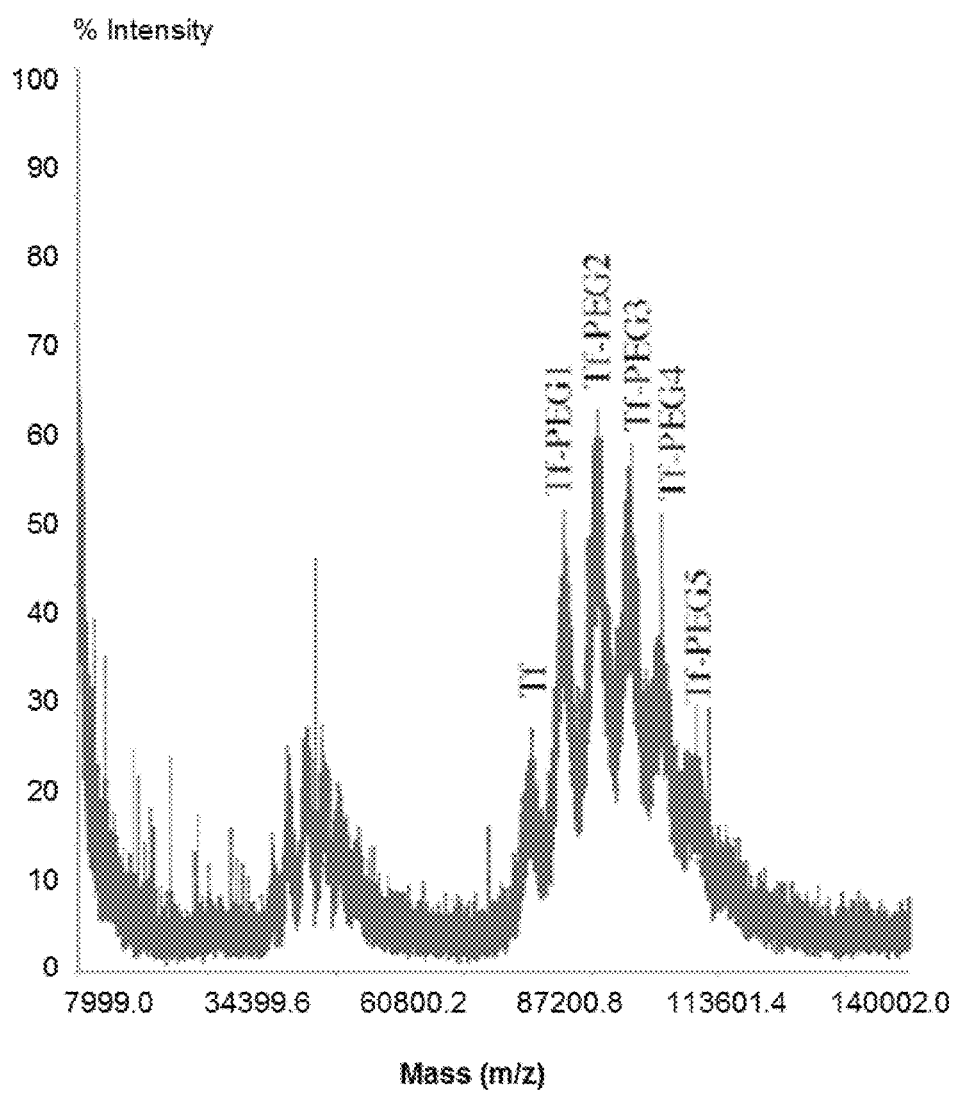
Figure 11B:
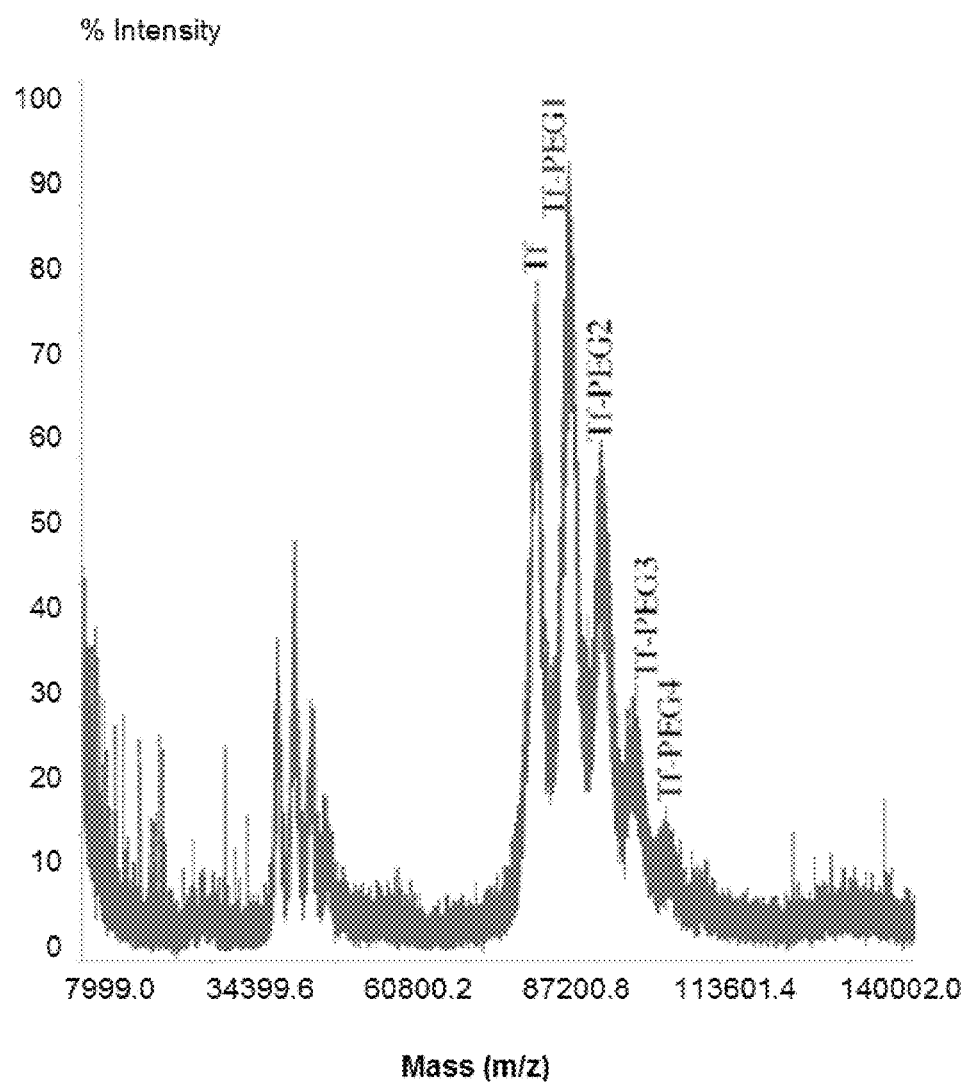
Figure 11C:
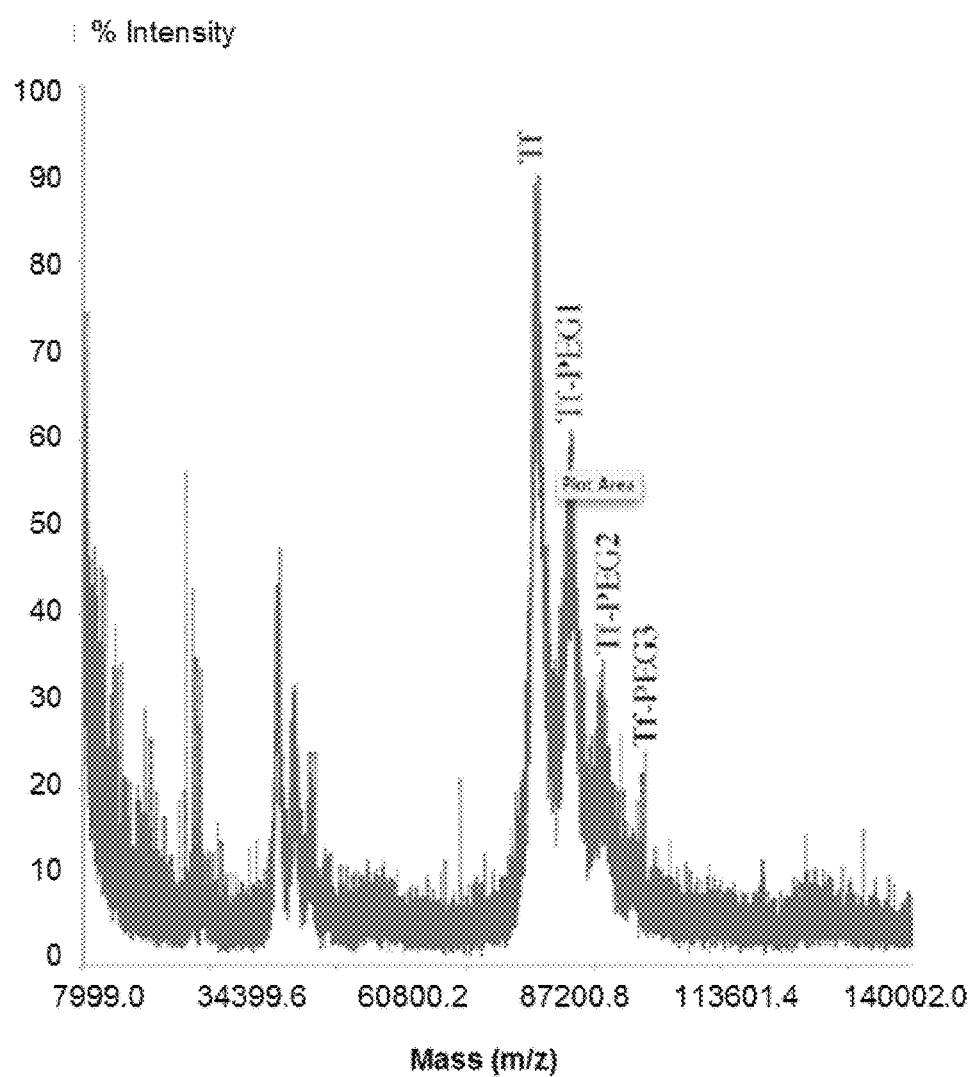
Figure 11E:
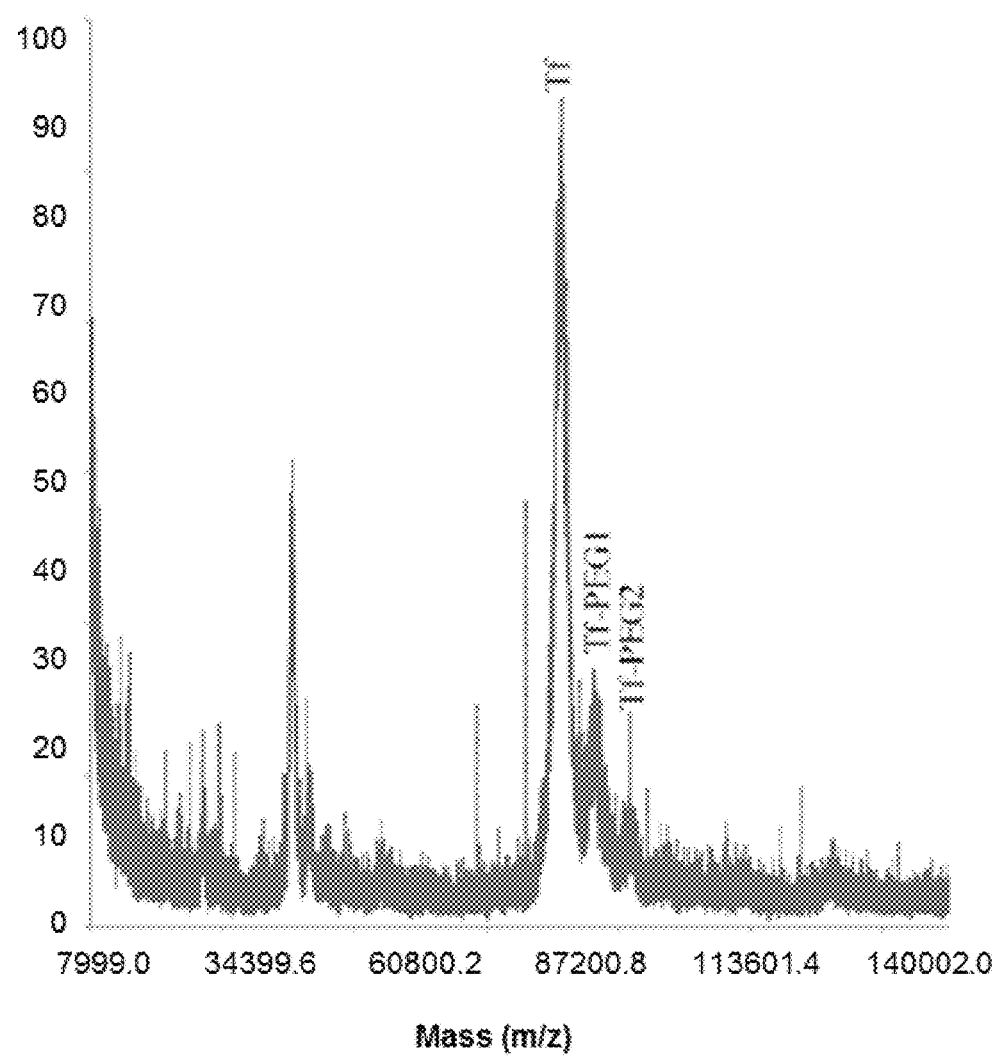
Figure 11F:
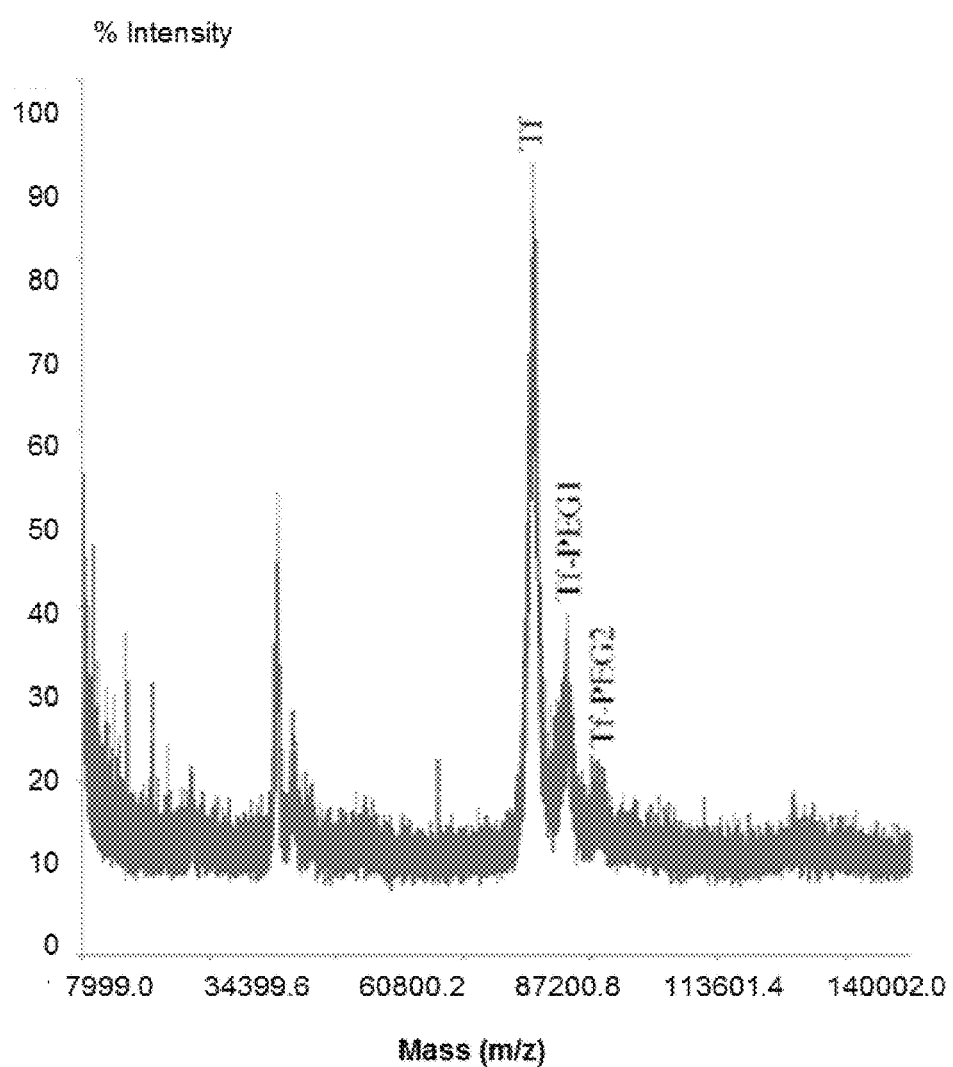

Preliminary studies were carried out to determine whether diamino ketal (DAK) could link Tf and PEG and allow for disassociation of Tf at mildly acidic pH. DAK was added to the amine-reactive terminus of NHS-PEG-OPSS followed by reaction with disuccinimidyl suberate (DSS) to reintroduce an amine-reactive functionality. DSS-DAK-PEG-OPSS was added to human holo-Tf to prepare Tf-DAK-PEG-OPSS (Scheme 2). Successful conjugation was verified by MALDI-TOF (FIG. 10). The conjugate's acid-sensitivity was verified by observing slow breakdown of the Tf-PEG's in the crude mixture over 24 hours in pH 5.5 buffer (FIG. 11). Significant decreases in higher orders of PEGylation are clear by 15 minutes and nearly all the PEG has cleaved by 2 hours.

Next, gold nanoparticles (Au—NP) were prepared with 120Tf-DAK-PEG molecules per nanoparticle. Nanoparticle characterization data for a typical batch of nontargeted (mPEG) and Tf-DAK-containing particles is shown in Table 2.

TABLE 2

NP characterization data for a typical batch. Average values from three measurements are given plus/minus one standard deviation for DLS diameter and zeta potential. The average mode from three measurements plus/minus one standard deviation is given for NTA.

|  | mPEG | 120Tf–DAK/particle |
| --- | --- | --- |
| Diameter DLS (nm) | 74.1 ± 0.8 | 77.2 ± 0.2 |
| Diameter NTA (nm) | 60.3 ± 0.7 | 63.0 ± 0.6 |
| Zeta potential (mV) | −7.79 ± 0.85 | −7.93 ± 0.60 |

Figure 12:
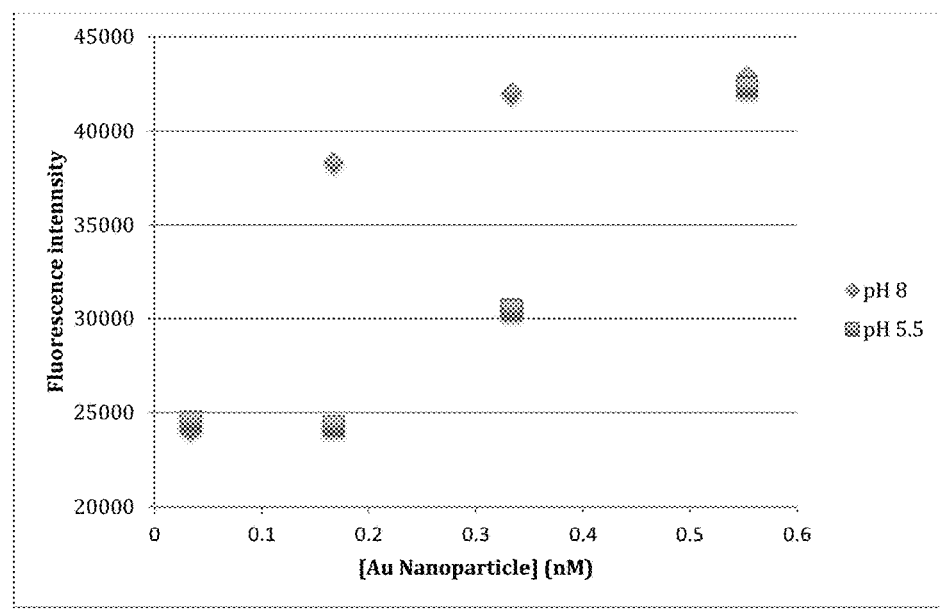
FIG. 12. Binding of Tf-DAK-PEG-Au nanoparticles to K562 cells after 1 hour incubation in buffer at either pH 5.5 (squares) or pH 8 (diamonds).

Tf-DAK AN-NPs were assessed for decreased avidity following incubation at acidic pH. Following 1 hour incubation at pH 5.5, Tf-DAK-PEG-Au NP's show much lower binding avidity to K562 cells (FIG. 12). The $K_d$ for particles left at pH 8 was 0.0294 nM while those at pH 5.5 was greater than 0.2 nM. This indicates less Tf was conjugated to the particles to bind to TfR on K562 cells after exposure to pH 5.5 buffer.

Figure 13:
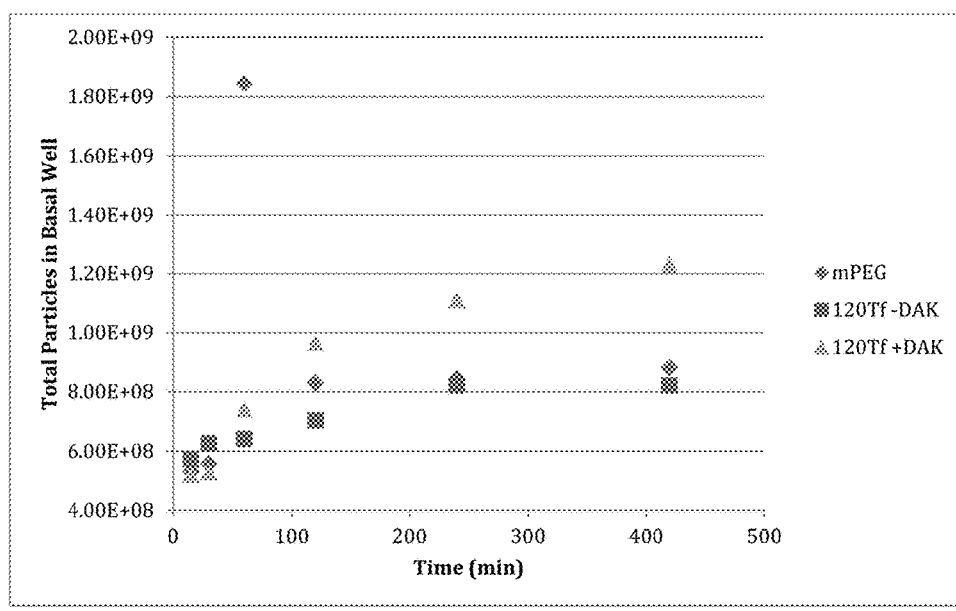
FIG. 13. Shows the migration of three different nanoparticles to the basal well of bEnd.3 coated Transwells® over time. Diamond plots reflect the migration of gold nanoparticles coated with mPEG only, square plots reflect the migration of gold nanoparticles coated with Tf-PEG without a pH cleavable DAK linker, and triangle plots show the migration of gold nanoparticles coated with Tf-PEG with a pH cleavable DAK linker.

In Vitro Transcytosis of Nanoparticles Having a Targeting Agent with a pH-Sensitive Linker Nanoparticle transcytosis of Tf-DAK AU-NPs was measured using bEnd.3 cells as a model for BBB endothelium. Cleavable, non-cleavable and non-targeted nanoparticles were each added to the apical chamber of bEnd.3-coated Transwells®. From 1 hour to 6 hrs, nanoparticles with cleavable Tf showed increased delivery to the basal well, while the non-cleavable and nontargeted particles showed similar capacity to one another to undergo transcytosis (FIG. 13, Table 3). These results indicate the presence of an acid-sensitive linker increases the capacity of nanoparticles to cross an in vitro model of the BBB. The measurement-to-measurement variability of the NTA method is still being Scheme 2: Synthesis of DSS—DAK—PEG—OPSS and its conjugation to Tf

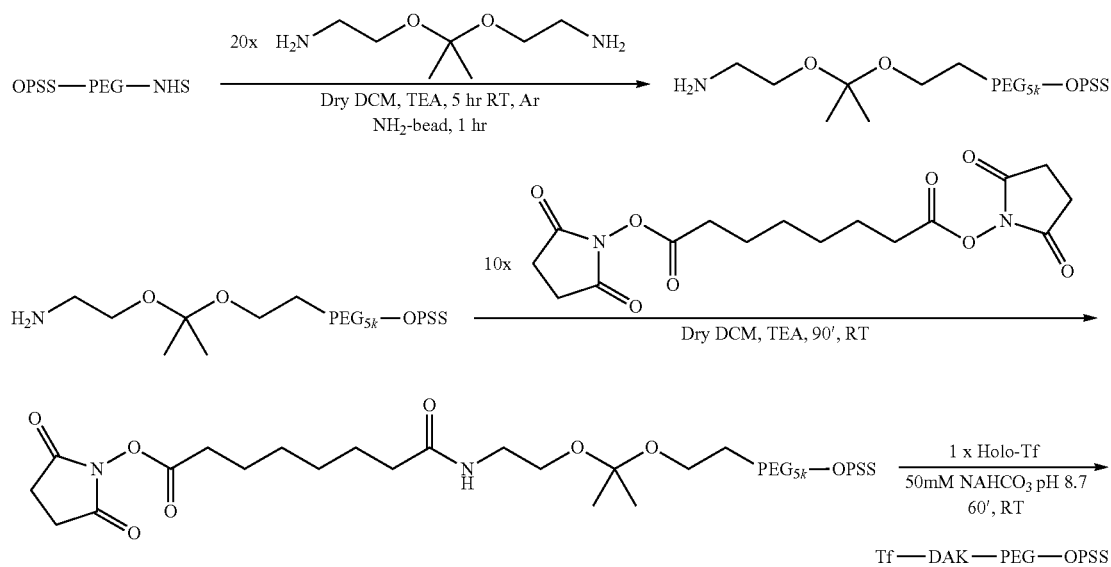

determined and potential outliers have been observed (e.g., the 60 min point for the mPEG sample in FIG. 13 and Table 3).

TABLE 3

Percentage of total NP's in the basal well over time for each formulation. A possible outlier is marked with an asterisk.

| | Formulation | | |
|---|---|---|---|
| Min | mPEG | 120Tf −DAK | 120Tf +DAK |
| 15 | 5.31 | 5.72 | 5.21 |
| 30 | 5.57 | 6.27 | 5.29 |
| 60 | 18.44* | 6.41 | 7.42 |
| 120 | 8.30 | 7.04 | 9.67 |
| 240 | 8.46 | 8.21 | 11.11 |
| 420 | 8.82 | 8.22 | 12.30 |

Figure 14:
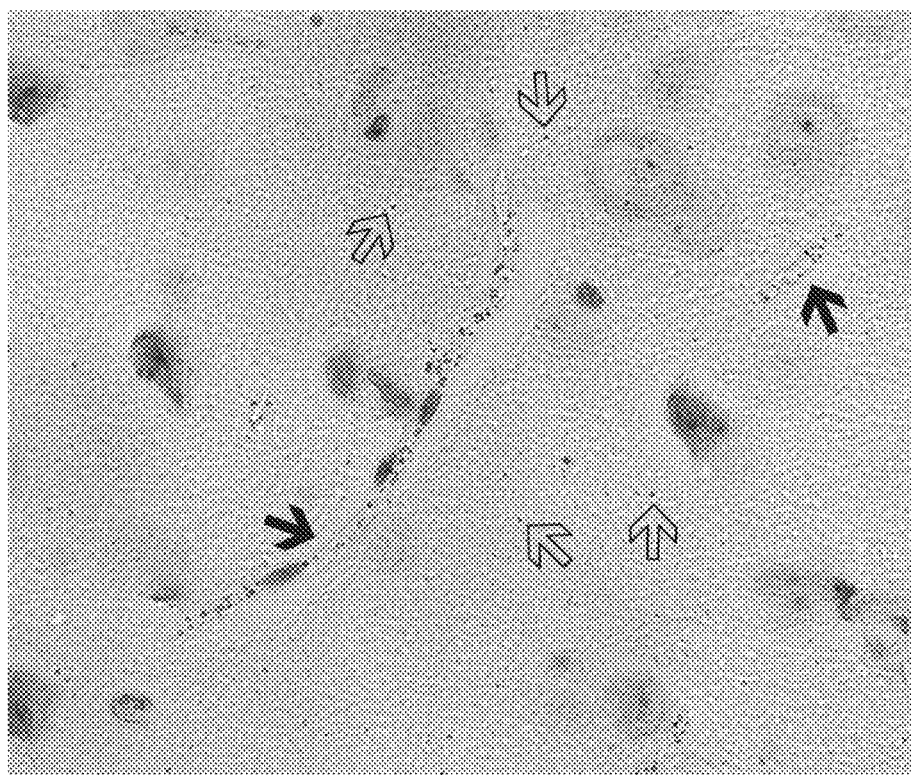
FIG. 14. Shows an image of a section from a mouse brain after treatment with the Tf containing gold nanoparticles that have an acid-cleavable linker. The solid arrows show NPs in the blood vessels and the open arrows NPs in the brain.

In Vivo Transcytosis of Nanoparticles Having a Targeting Agent with a pH-Sensitive Linker Gold nanoparticles containing 120Tf-DAK-PEG molecules per particle were injected into a BALB/c mouse via lateral tail vein injection. The brain was isolated 12 hours after injection, fixed and sectioned, and stained with silver enhancement solution. Gold nanoparticles were identified as distinct, individual black dots by light microscopy (FIG. 14). Nanoparticles identified distinctly beyond the borders of blood vessels were determined to be nanoparticles within the brain parenchyma. Large amounts of nanoparticles were identified within the parenchyma, indicating the presence of the acid-cleavable link increased the ability of the nanoparticles to cross the BBB.

Example III—Delivery of a Therapeutic Agent to the Brain Using Nanoparticles Having a Targeting Agent with a pH-Sensitive Linker One drug that has therapeutic interest and experimental utility for neurological disorders is dopamine. Parkinson's disease is characterized by breakdown of dopaminergic neurons in the substantia nigra within the midbrain. This leads to decreased levels of dopamine within the midbrain and a range of clinical symptoms including rigidity, bradykinesia, tremor and neuropsychiatric changes. Dopamine cannot be used to treat the disease directly because it is incapable of crossing the BBB.

PLGA nanoparticles with the same cleavable ligand density, hydrodynamic diameter and zeta potential as the optimal Au—NP formulation will be prepared and loaded with $^3$H-labeled dopamine. The particles will be administered intravenously to mice and dopamine quantitated using the intravenous-injection technique, the gold standard for measuring a drug's ability to cross the BBB. Free dopamine can be used as a negative control since it is restricted to the blood stream. The amount of dopamine that accumulates in the parenchyma will be compared to concentrations of L-DOPA—a dopamine prodrug that can cross the BBB and is currently used for Parkinson's treatment—that reach the brain after systemic administration.

The PLGA particle should be able to deliver more dopamine to the CNS than free drug alone. Particle dose can be adjusted to be sufficiently high to reach therapeutically useful quantities. Targeting and initiation of transcytosis is dependent on Tf-TfR interactions, so once the NP reaches the BBB endothelium the PLGA particles should behave similarly to the Au-NP's; however, it is unknown whether a lower-density nanoparticle core, such as PLGA, will affect nanoparticle flow in the bloodstream and affect the rate of surface Tf-TfR interactions at the BBB. This may require optimization of Tf-ligand density and/or dosing quantity to increase—or decrease—Tf-TfR interactions and lead to the greatest amount of transcytosis.

Methods

Unless stated otherwise the following methods were used to carry out the experiments described in the previous examples.

PLGA-PEG-S-S-PEG-Tf Nanoparticle Preparation, Characterization and Analysis Preparation of Intra-PEG Disulfide Bond.

Amine-PEG-thiol ($NH_2$-PEG-SH, 3.4 kDa) was dissolved in DMF at a concentration of 20 mg/mL. Carboxy-PEG-thiol (COOH-PEG-SH, 2 kDa) was added at an equimolar concentration (Scheme 1). Hydrogen peroxide ($H_2O_2$) was added to give a final concentration of 3% $H_2O_2$. The reaction mixture was stirred at room temperature for 24 hours and analyzed by MALDI-TOF. Disulfide bonds were confirmed to link the PEG polymers by adding 1000× molar excess beta-mercaptoethanol to the polymer and validating by MALDI-TOF that the disulfide cleaved and polymers disassociated.

Synthesis of PLGA-PEG Block Copolymers (Scheme 3).

PLGA-NHS was prepared by dissolving 250 mg carboxy-terminated poly(D,L-lactic-co-glycolic acid) (50/50) (PLGA-COOH) in 1.1 mL of acetonitrile. Ten molar excess 1-ethyl-3-(3-dimethylaminopropyl)carbodiimide (EDC) and N-hydroxysuccinimide (NHS) were added to this solution and stirred for 90 minutes at room temperature. The product was precipitated out of solution by addition of 30 mL of methanol followed by centrifugation at 2700 g for 10 minutes. The supernatant was discarded and the product was washed with 30 mL of methanol and collected again by centrifugation. This process was repeated twice more for a total of three washes. The purified PLGA-NHS was dried under vacuum.

Various hetero-bifunctional polyethylene glycol (PEG) polymers were added to PLGA-NHS to form PLGA-PEG block copolymers. All PEG polymers contained an amine terminus to react with the NHS ester on the PLGA polymer and either a carboxyl ($NH_2$-PEG-COOH; 5kDa); methoxy ($NH_2$-PEG-OCH$_3$, 5kDa); or sulfhydryl ($NH_2$-PEG-SH; 3.4 kDa) terminus at the other end. Dried PLGA-NHS was dissolved in acetonitrile at a concentration of 5 mM followed by addition of 1.5× molar excess hetero-bifunctional PEG and 10× molar excess N,N-diisopropylethanolamine (DIPEA). The product was precipitated by addition of 30 mL diethyl ether after 24 hours at room temperature with gentle stirring. The PLGA-PEG block copolymer was collected by centrifugation at 2700 g for 10 minutes. The supernatant was discarded and the product was washed with another 30 mL of ether and collected again by centrifugation. This process was repeated twice more for a total of three washes. The product was dried under vacuum.

Scheme 3. Synthesis of PLGA—PEG block coplymer. The chemical group labeled 'R' in the heterobifunctional PEG polymer in step two corresponds to a methoxy group, a carboxylic acid or a free thiol.

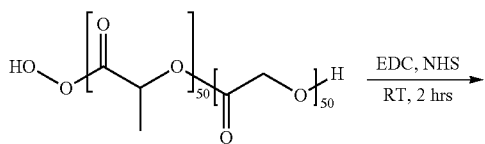

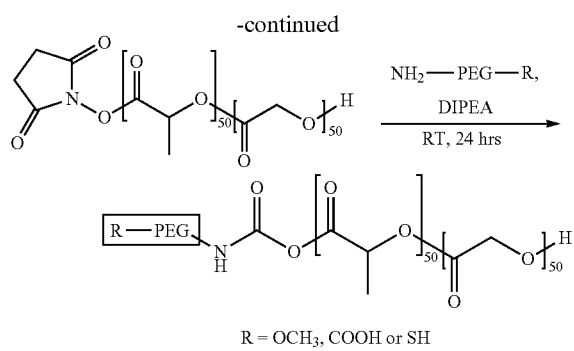

R = OCH₃, COOH or SH

Synthesis of Disulfide-Containing PLGA-PEG Copolymer (Scheme 4).

PLGA-PEG-S—S-PEG-COOH was prepared by dissolving 100 mg of PLGA-PEG-SH in 2 mL of DMF. To this was added 5× molar excess SH-PEG-COOH (2 kDa). Following dissolution of the SH-PEG-COOH, 200 uL of 30% hydrogen peroxide ($H_2O_2$) was added to the reaction mixture to give a final concentration of 3% $H_2O_2$. The reaction was left stirring at room temperature for 24 hours.

Scheme 4. Synthesis of disulfide-containing PLGA—PEG polymer.

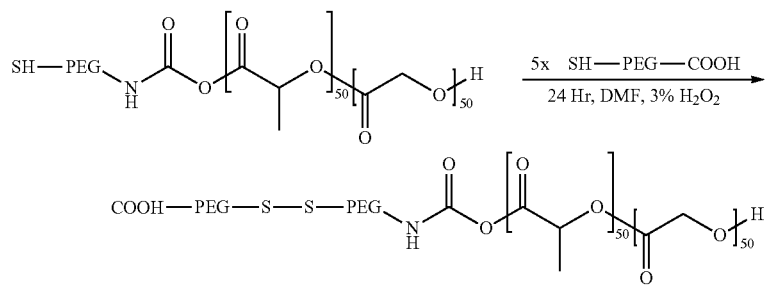

Synthesis of PLGA-AF488.

Fluorescently-labeled PLGA polymer was prepared by dissolved 50 mg of PLGA-NHS in 1 mL of DMF followed by addition of 1 mg of Alexa-fluor 488 cadaverine (AF488) dissolved in 0.5 mL of DMF. The product was collected after one hour by precipitation with 20 mL of methanol followed by centrifugation at 2700 g for 10 minutes. The product was washed in another 20 mL of methanol and collected again by centrifugation. This process was repeated twice more for a total of three washes. The purified product was dried under vacuum.

Preparation of PLGA-PEG Nanoparticles (Scheme 5).

Figure 16A:
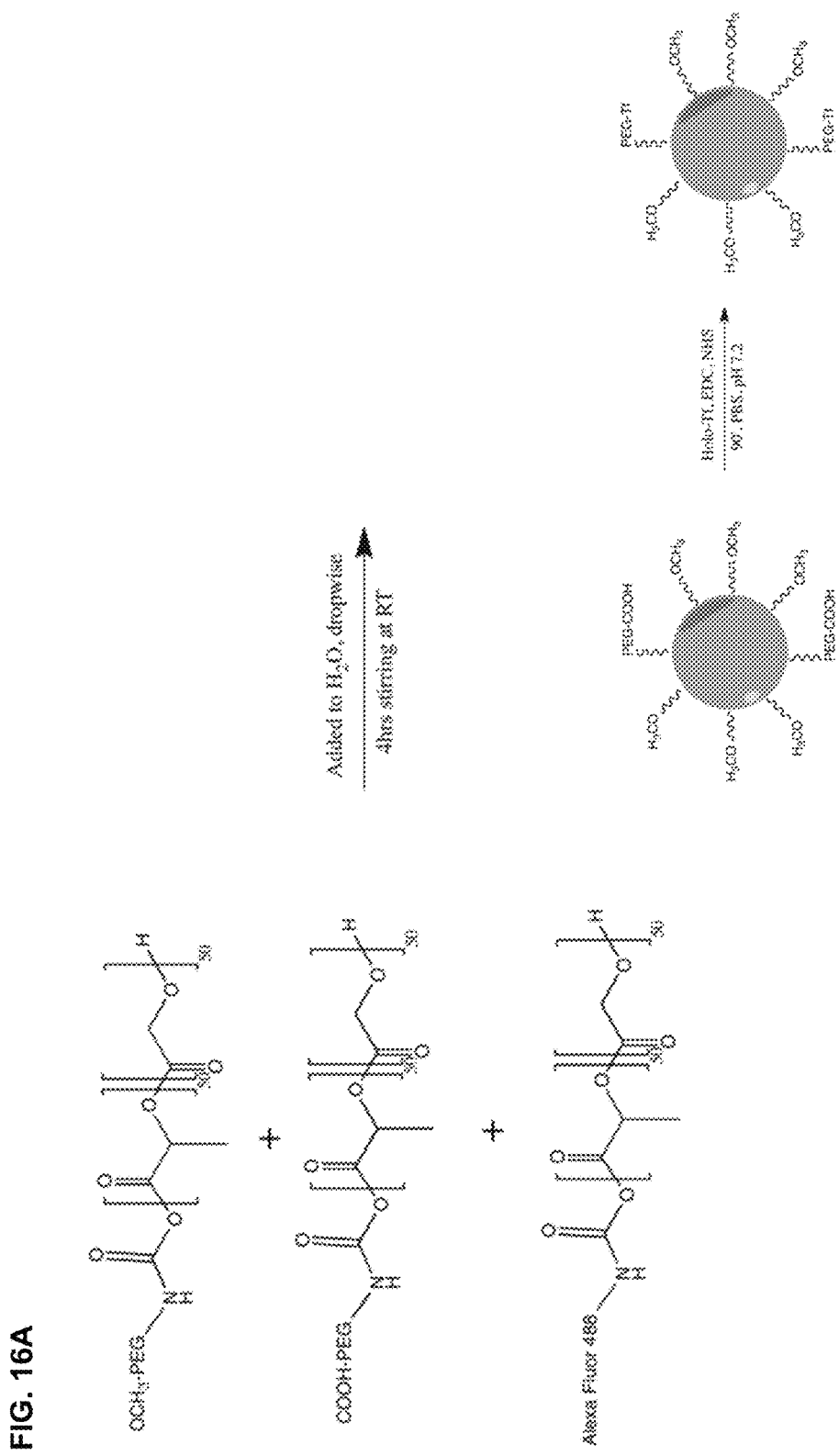
FIG. 16A shows the preparation of non-cleavable nanoparticles.

PLGA-PEG nanoparticles were prepared by nanoprecipitation (FIG. 16). Various combinations of PLGA-PEG block copolymers were dissolved in 3 mL DMF at a total concentration of 10 mg/mL PLGA-PEG copolymer. Each formulation contained 2.5% PLGA-AF488 by weight. The polymer mixture was added dropwise to 30 mL of stirring water and allowed to mix for 2 hours. The resulting nanoparticle mixture was passed through a 0.2 μm filter and purified through ultrafiltration with a 50 kDa MWCO centrifugal filter at 2700 g for 10 minutes. The nanoparticle retentate was resuspended in 10 mL of water and collected by ultrafiltration twice more for a total of three washes. Following the final wash cycle, the concentrated nanoparticles were resuspended in 1 mL of PBS. The relative amounts of each polymer used to make the four different nanoparticle formulations are shown in Table 4. Each formulation contained 2.5% PLGA-AF488.

TABLE 4

| Formulation | % PLGA-mPEG | % PLGA-PEG-COOH | % PLGA-PEG-S-S-PEG-COOH |
|---|---|---|---|
| mPEG | 100 | 0 | 0 |
| Low Tf | 90 | 10 | 0 |
| High Tf | 70 | 30 | 0 |
| High Tf + S-S | 70 | 0 | 30 |

Addition of Human Holo-Transferrin to Nanoparticles.

Nanoparticle concentration was determined using nanoparticle tracking analysis (NTA). Nanoparticle formulations were diluted to 0.0001 mg/mL in PBS and the particle concentration was determined using a Nanosight NS500. EDC and NHS were added to the nanoparticles at 10× molar excess to the total amount of carboxy-terminated PLGA-PEG block copolymer (PLGA-PEG-COOH or PLGA-PEG-S—S-PEG-COOH) present in the formulation and allowed to stir at room temperature for 10 minutes. Based on the nanoparticle concentration determined by NTA, human holo-transferrin (Tf) prepared in PBS, pH 7.2 was added at 30× molar excess for the low-Tf formulations and 300× molar excess for the high-Tf and disulfide-containing formulations. The reaction mixture was stirred for 90 minutes at room temperature and then purified by ultrafiltration with a 100 kDa MWCO centrifugal filter at 3000 g for 10 minutes. The nanoparticle retentate was resuspended in 0.5 mL of PBS and collected again by ultrafiltration. This process was repeated twice more for a total of three washes.

Characterization of PLGA-PEG Nanoparticles.

Particle sizes and zeta potentials were measured with a Brookhaven Instruments DLS and ZetaPALS. Particle diameter was measured in PBS over 2 minutes. Zeta potentials were taken in 1.5 mM KCl (pH 7.0) and averaged from 3 runs at target residual of 0.018.

In Vitro Determination of Disulfide-Containing Nanoparticle Binding Affinity.

Neuro2A cells were cultured in DMEM, 10% FBS and penicillin/streptomycin. Prior to incubation with nanoparticles, cells were fixed in BD Cytofix® for 15 minutes at 4° C., washed and resuspended in PBS+4% BSA. Various concentrations of the nanoparticle formulations were incubated with $2 \times 10^6$ cells at $1 \times 10^6$ cells/mL for 90 minutes. In order to cleave the disulfide-bond present in the disulfide-containing nanoparticle formulation, these particles were treated with dithiothreitol (DTT) for 30 minutes at room temperature prior to addition to the Neuro2A cells. Excess DTT was removed by washing the nanoparticles in PBS and collecting them by ultrafiltration. Cells were pelleted at 200 g for 5 minutes and resuspended in 200 uL PBS. Nanoparticle binding was determined by measuring fluorescence intensity at 488 nm excitation, 525 nm emission. The data were fit to the Langmuir binding isotherm with $B_{max}$ and $K_D$ numerically determined using Matlab function nlinfit.

Animal Studies.

All animals were treated according to the NIH Guidelines for Animal Care and Use approved by the Caltech Institutional Animal Care and Use Committee. Nanoparticle formulations containing $1 \times 10^{10}$ to $1 \times 10^{11}$ particles were prepared in 150 uL of PBS and injected into female BALB/c mice via lateral tail vein. The mice were sacrificed one hour after injection by $CO_2$ asphyxiation. The brain was removed and fixed in 4% paraformaldehyde overnight for further tissue processing.

Confocal Microscopy.

Formaldehyde-fixed tissues were embedded in paraffin, sectioned and deparaffinized. The tissue was mounted using Prolong Gold® Antifade Reagant with DAPI (nuclear stain). Sections were imaged on a Zeiss LSM 510 inverted confocal scanning microscope with a Zeiss PlanNeofluar 40x/1.3 oil objective. The excitation wavelength for DAPI was 710 nm (two-photon laser) and 488 nm for Alexafluor 488 labeled nanoparticles. Their corresponding emission filters were 390-465 nm and 530-560 nm respectively.

Synthesis of Ketal-Containing PEG (DSS-DAK-PEG-OPSS):

Diamino ketal (DAK; FIG. 4) was incorporated between Tf and PEG. In brief, 150 mg OPSS-PEG-NHS (5kDa, Laysan Bio) was dissolved in dry DCM. To this was added 20x molar excess TEA and 20x DAK (Sigma Aldrich). The solution was stirred for 5 hours under argon at room temperature. Presoaked N-(2-Aminoethyl)aminomethyl polystyrene beads ($NH_2$-bead, EMD Millipore) were added at 10x molar excess to DAK and stirred for one hour under the same conditions. The solution was filtered and precipitated by addition of 150 mL diethyl ether. After sitting at room temperature for 15 minutes, the precipitate was isolated by centrifugation at 3220 g for 15 minutes. The solid was washed with ether and collected by centrifugation twice more. The product was dried under vacuum to yield a dense, white solid. The resulting DAK-PEG-OPSS (100 mg) was dissolved in dry DCM. Disuccinimidyl suberate (DSS, Pierce) and TEA were added at 10x molar excess. The reaction was stirred at room temperature for 90 minutes. The product was precipitated by addition of 60 mL ether. After sitting at room temperature for 30 minutes, the precipitate was isolated by centrifugation at 3220 g for 15 minutes. The solid was washed with ether and collected by centrifugation twice more. It was dried under vacuum to yield a dense, white solid.

Conjugation of DSS-DAK-PEG-OPSS to Tf:

Human holo-Tf (20 mg) was dissolved in 900 uL 100 mM $NaHCO_3$ pH 8.5. DSS-DAK-PEG-OPSS (2x molar excess) was dissolved in 100 uL DMSO and added to the Tf. The solution sat at room temperature for 60 min with light agitation. Excess PEG was removed and the reaction was quenched by centrifugation through a 50 kDa MWCO spin filter (EMD Millipore) at 14000 g for 5 minutes. The retentate was washed with 10 mM $NaH_2PO_4$ pH 8.0 twice more. Conjugation was verified by MALDI-TOF using a sinapinic acid matrix.

Purification of Tf-DAK-PEG-OPSS:

Higher orders of PEGylation were removed from the mixture by hydrophobic interaction chromatography (HIC) on a AKTA Prime Plus FPLC System (GE Healthcare, 5 mL HiTrap Phenyl column) using a high salt buffer of 1M ammonium sulfate with 50 mM sodium phosphate pH 7.5 and an elution buffer consisting of the latter salt only. The amount of mono-PEGylated Tf remaining in the mixture was determined by dipyridyl disulfide cleavage assay. The Tf-PEG mixture was diluted in PBS pH 7.2 with 5 mM EDTA and the absorbance at 343 nm was recorded. Dithiothreitol (DTT) was added to give a final concentration of 1.5 mg/mL. After 15 minutes at room temperature, the absorbance at 343 nm was recorded again. The difference in absorbance was used to calculate the amount of OPSS present in the mixture and, subsequently, the amount of Tf-DAK-PEG-OPSS. Iron citrate in 100 mM NaHCO3 pH 8.6 was added at 2.5x molar excess to the mono-PEGylated fraction and incubated for 60 minutes at room temperature with light stirring. The excess iron was removed with six washes of 100 mM sodium bicarbonate through a 50 kDa centrifugal filter. The iron loading content of Tf was measured by UV-VIS through the ratio of A465/A280 and was compared to the same ratio of the original non-processed holo-Tf. A465/A280 ratios above 0.8 were considered to be adequate evidence for iron loading.

Estimation of Tf-DAK-PEG-OPSS Half-Life at pH 5.5:

Tf-DAK-PEG-OPSS was diluted to 1 mg/mL in 100 mM NaOAc pH 5.5 at 37° C. At various time points, aliquots were removed, diluted 1:10 in 10 mM $NaH_2PO_4$ pH 8.0 and frozen on $CO_2(s)$. Once the last aliquot was removed, all samples were melted and immediately measured by MALDI-TOF using a sinapinic acid matrix.

Synthesis and Purification of Tf-PEG-OPSS:

OPSS-PEG-NHS (5 kDa, Laysan Bio) was added to human holo-Tf (20 mg) at an 8x molar excess in 1 mL 100 mM $NaHCO_3$ pH 8.5. The reaction sat at room temperature for 90 minutes under light agitation. Excess PEG was removed and the reaction was quenched by centrifugation through a 50 kDa MWCO spin filter (EMD Millipore) at 14000 g for 5 minutes. The retentate was washed with 10 mM $NaH_2PO_4$ pH 8.0 twice more. Conjugation was verified by MALDI-TOF using a sinapinic acid matrix. The monoPEGylated fraction was isolated by HPLC (1200 series, Agilent, using two TOSOH TSK gel G3000swxl columns in series) and verified by MALDI-TOF using a sinapinic acid matrix.

Preparation of Tf-DAK-PEG-Au Nanoparticles:

Either Tf-DAK-PEG-OPSS or Tf-PEG-OPSS was added to gold nanoparticles with 50 nm diameter (BBI International) at 120x molar excess. The solution was stirred vigorously for 90 minutes. mPEG-SH (5kDa, Laysan Bio) was added at 10,000x excess and stirred for another 60 minutes. The particles were collected by centrifugation at 20,000 g for 10 minutes, washed with $dH_2O$ and sonicated briefly. This process was repeated twice more to give three total washes. After the final centrifugation, the particles were resuspended in 10 mM $NaH_2PO_4$ pH 8.0. To prepare untargeted particles (Au-mPEG), only mPEG-SH was added to 50 nm gold cores for 60 minutes with vigorous stirring. The particles were purified as described above.

Nanoparticle Characterization:

Nanoparticle were diluted in PBS and hydrodynamic diameter was measured using dynamic light scattering (DLS) and nanotracking analysis (NTA). Particle concentration (particles/mL) was also determined by NTA using the average of three measurements in the same sample. Zeta potential was measured by DLS in 1.5 mM KCl (pH 7.0) using a target residual of 0.02.

Nanoparticle Binding Affinity to K562 Cells:

K562 cells were grown at 37° C., 5% $CO_2$ in DMEM+ 10% FBS with penicillin/streptomycin. Cells were washed with PBS and removed using a cell scraper. After centrifugation at 300 g for 3 minutes, the cells were fixed using BD Cytofix (BD Biosciences) for 20 minutes at 4° C. The cells were washed and resuspended in PBS+4% BSA. Tf-DAK-PEG-Au NP's containing 120Tf/particle were incubated for one hour at 37° C. in either 100 mM NaOAc pH 5.5 or 100 mM $NaHCO_3$ pH 8.5. The particles were collected by centrifugation at 20,000 g for 10 minutes and resuspended in PBS+4% BSA. Increasing concentrations of nanoparticles were added to 1e6 cells at 5e6 cells/mL and sat at RT for 90 minutes. The cells were centrifuged at 300 g for 3 minutes washed twice with 15 mL PBS. Finally, the cells were stained with silver enhancement solution (Ted Pella), developed for 15 minutes and fluorescence read (310 nm excitation, 400 nm emission) using a plate reader (Tecan, infinite M900). Data were fit to the Langmuir binding isotherm using nlinfit in Matlab and $K_D$ was calculated.

Figure 15:
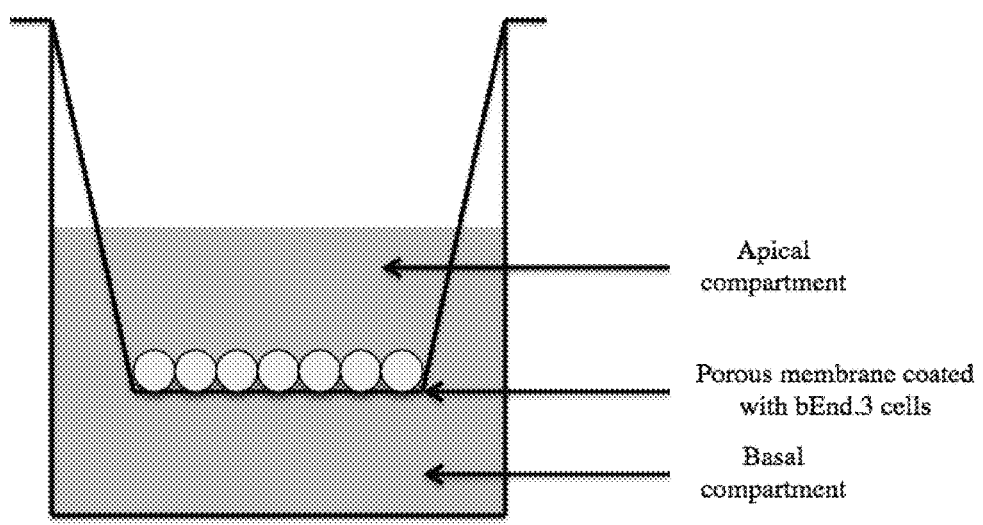
FIG. 15. A schematic representation of a tissue culture Transwell® system.

Nanoparticle Transcytosis Across bEnd.3 Cells:

bEnd.3 cells were grown in 37° C., 5% $CO_2$ in DMEM+ 10% FBS with penicillin/streptomycin. The cells were seeded on 12 mm PET-coated Transwell® supports (Corning) at 82,500 cells/well. Media was replaced in the apical and basal wells every three days. Transepithelial electrical resistance (TEER) was measured in an Endohm chamber and using an EVOM resistance meter (World Precision Instruments). Once TEER had reached ≥30 Ohms*cm², transcytosis experiments were performed. Cleavable, non-cleavable and non-targeted particles were added at 1e10 particles/well to the apical well. At various time points, 50 uL was removed from the basal well and replaced with fresh media. The aliquot was diluted to 250 uL using PBS and nanoparticle concentration was measured using NTA. A running tally of total nanoparticles in the apical well was calculated and used to determine transcytosis capacity (FIG. 15).

Tf-DAK-PEG-Au Nanoparticle Injection into BALB/c Mice.

All animals were treated according to the NIH Guidelines for Animal Care and Use as approved by the Caltech Institutional Animal Care and Use Committee. A total of 4.5×10¹¹ gold nanoparticles containing 120 Tf-DAK-PEG molecules per particle were prepared as previously described. Following purification, the particles were suspended in 150 uL PBS pH 7.4 and injected into the lateral tail vein of a female BALB/c mouse (Jackson laboratory). The mouse was euthanized twelve hours after injection by CO2 asphyxiation. The brain was immediately removed and placed in 10% neutral buffered formalin and stored overnight at 4° C. The brain was then dehydrated in increasing concentrations of ethanol (3×30 minutes each), equilibrated in xylenes (3×30 minute washes) and equilibrated in 50% xylene/50% molten paraffin (30 minutes). The tissues were placed in pure molten paraffin (3×1 hour), placed in a paraffin mold, allowed to cool, and 5 um sections were obtained. Sections were deparafinized with xylenes, rehydrated with serial dilutions of ethanol. Nanoparticles were visualized by staining with silver enhancement solution (Ted Pella) according to the manufacturer's guidelines. The tissue was dehydrated with increasing amounts of ethanol and xylenes and mounted with Permount (Fisher). All light microscopy images were taken on an Olympus IX50 microscope with a 40× objective using QCapture Pro imaging software (QImaging).

What is claimed:

1. A method of delivering a therapeutic agent or imaging agent to a patient, the method comprising administering to the patient a nanoparticle comprising a nanoparticle core having a surface; wherein the nanoparticle further comprises (a) the therapeutic agent or the imaging agent and (b) a targeting agent, the targeting agent comprising a linker and a targeting ligand attached to the surface of the nanoparticle core by the linker;

the targeting ligand having an affinity for binding to a receptor expressed by endothelial cells of the blood brain barrier;

the surface of the nanoparticle core comprises a cationic mucic acid polymer (cMAP), poly(lactic-co-glycolic acid) (PLGA), chitosan, or a polyethyleneimine; and the linker comprising a polyethylene glycol (PEG) moiety conjugated to the surface of the nanoparticle core by a pH sensitive linkage selected from the group consisting of diamino ketal or imine linkage, wherein the linker is dissociable at a pH in a range of from about 6.8 to about 2.0.

2. The method of claim 1, wherein the targeting ligand comprises transferrin, an antibody specific for the transferrin receptor, a polypeptide that specifically binds to the transferrin receptor, insulin, an antibody specific for the insulin receptor, a polypeptide that specifically binds to the insulin receptor, insulin-like growth factor 1, an antibody specific for the insulin-like growth factor receptor 1, a polypeptide that specifically binds to the insulin-like growth factor receptor 1, apolipoprotein E, angiopep-2, an antibody specific for low density lipoprotein receptor or lipoprotein receptor-related protein, a polypeptide that specifically binds to low density lipoprotein receptor or lipoprotein receptor-related protein; an antibody specific for diphtheria toxin receptor, or a polypeptide that specifically binds to diphtheria toxin receptor.

3. The method of claim 2, wherein the surface of the nanoparticle core comprises a cationic mucic acid polymer (cMAP).

4. The method of claim 3, wherein the nanoparticle core comprises cationic mucic acid polymer (cMAP) having the structure:

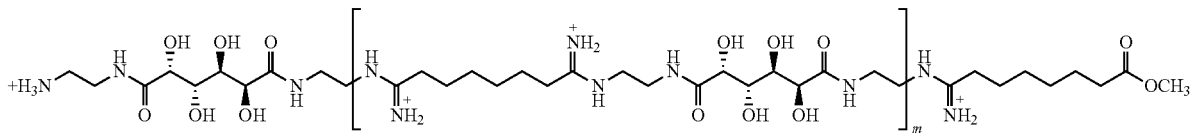

wherein m is any whole number between 5 and 50.

5. The method of claim 2, wherein the nanoparticle comprises the therapeutic agent, the therapeutic agent comprising serotonin or dopamine.

6. The method of claim 2, wherein the surface of the nanoparticle core comprises poly(lactic-co-glycolic acid) (PLGA) polymers.

7. The method of claim 2, wherein the linker comprises a diamino ketal conjugated to the PEG.

8. The method of claim 1, wherein the linker further comprises a disulfide bond.

9. The method of claim 1, wherein the linker further comprises a polypeptide bond.

10. The method of claim 1, wherein the pH sensitive linkage dissociates at a pH in a range of from about 5.5 to about 2.5.

11. The method of claim 1, wherein the pH sensitive linkage dissociates at a pH in a range of from about 5.5 to about 4.0.

12. The method of claim 1, wherein the linker comprises an imine linkage conjugated to the PEG.

13. The method of claim 1, wherein the nanoparticle comprises up to 200 targeting agents conjugated to its surface.

14. The method of claim 1, wherein the nanoparticle comprises less than 5 targeting agents conjugated to its surface.

15. The method of claim 1, wherein the nanoparticle comprises a single targeting agent conjugated to its surface.

16. The method of claim 1, wherein the nanoparticle has:
   (a) an average particle size of from about 40 nm to about 100 nm as measured by dynamic light scattering (DLS);
   (b) an average zeta potential of from about −0.5 mV to about −15.0 mV as measured by phase analysis light scattering; or
   (c) both (a) and (b).

17. The method of claim 1, wherein the nanoparticle comprises the therapeutic agent.

18. The method of claim 17, wherein the therapeutic agent is effective against a neurological disorder.

19. The method of claim 17, wherein the therapeutic agent is serotonin or dopamine.

20. The method of claim 1, wherein the nanoparticle further comprises the imaging agent.

21. The method of claim 20, wherein the imaging agent is Cu-64.

22. The method of claim 1, wherein systemically administering comprises administering parenterally, intravenously, or intraperitoneally.

23. The method of claim 1, wherein the patient suffers from a neurodegenerative disease.

24. The method of claim 1, wherein the patient suffers from Alzheimer's disease, Huntington's disease, Parkinson's disease, and multiple sclerosis.

* * * * *